(12) United States Patent
Bitinaite et al.

(10) Patent No.: US 9,034,597 B2
(45) Date of Patent: May 19, 2015

(54) DETECTION AND QUANTIFICATION OF HYDROXYMETHYLATED NUCLEOTIDES IN A POLYNUCLEOTIDE PREPARATION

(75) Inventors: Jurate Bitinaite, Rowley, MA (US); Romualdas Vaisvila, Ipswich, MA (US); Sriharsa Pradhan, Wenham, MA (US); Yu Zheng, Topsfield, MA (US); Richard J. Roberts, Wenham, MA (US); Devora Cohen-Karni, Cambridge, MA (US); Christopher Noren, Boxford, MA (US); Elisabeth A. Raleigh, Somerville, MA (US); Geoffrey Wilson, South Hamilton, MA (US); Hang-Gyeong Chin, South Hamilton, MA (US)

(73) Assignee: New England Biolabs, Inc., Ipswich, MA (US)

( * ) Notice: Subject to any disclaimer, the term of this patent is extended or adjusted under 35 U.S.C. 154(b) by 69 days.

(21) Appl. No.: 13/392,286

(22) PCT Filed: Aug. 25, 2010

(86) PCT No.: PCT/US2010/046632
§ 371 (c)(1),
(2), (4) Date: Mar. 12, 2012

(87) PCT Pub. No.: WO2011/025819
PCT Pub. Date: Mar. 3, 2011

(65) Prior Publication Data
US 2012/0156677 A1    Jun. 21, 2012

Related U.S. Application Data

(60) Provisional application No. 61/275,136, filed on Aug. 25, 2009, provisional application No. 61/254,346, filed on Oct. 23, 2009, provisional application No. 61/354,826, filed on Jun. 15, 2010, provisional application No. 61/370,037, filed on Aug. 2, 2010.

(51) Int. Cl.
C12Q 1/68    (2006.01)

(52) U.S. Cl.
CPC .................................... *C12Q 1/6827* (2013.01)

(58) Field of Classification Search
None
See application file for complete search history.

(56) References Cited

U.S. PATENT DOCUMENTS

| 6,692,916 B2 | 2/2004 | Bevilacqua et al. |
| 6,960,439 B2 | 11/2005 | Bevilacqua et al. |
| 7,662,563 B2 | 2/2010 | Gonzalgo et al. |
| 2005/0233340 A1* | 10/2005 | Barrett et al. ............ 435/6 |
| 2009/0317801 A1 | 12/2009 | Van Den Boom et al. |
| 2010/0151468 A1 | 6/2010 | Esteller et al. |
| 2010/0167942 A1* | 7/2010 | Zheng et al. ............ 506/8 |
| 2010/0172880 A1 | 7/2010 | Laird et al. |
| 2011/0183320 A1 | 7/2011 | Flusberg et al. |
| 2011/0236894 A1* | 9/2011 | Rao et al. ............ 435/6.11 |
| 2011/0301045 A1 | 12/2011 | He et al. |
| 2012/0064521 A1 | 3/2012 | Yen et al. |

FOREIGN PATENT DOCUMENTS

| EP | 2365067 | 9/2011 |
| WO | 02/101013 A2 | 12/2002 |
| WO | 2010037001 | 4/2010 |
| WO | 2010075375 A1 | 7/2010 |
| WO | 2011/091146 | 7/2011 |

OTHER PUBLICATIONS

Valinluck et al. (2007) Endogenous Cytosine Damage Products Alter the Site Selectivity of Human DNA Maintenance Methyltransferase DNMT1. Cancer Research, 67:946-950.*
Monod et al. (1997) The Genome of the Pseudo T-even Bacteriophages, a Diverse Group that Resembles T4. Journal of Molecular Biology, 267:237-249.*
Frigola et al. (2002) Methylome profiling of cancer cells by amplification of inter-methylated sites (AIMS). Nucleic Acids Research, 30(7):e28, pp. 1-7.*
de Kort et al. (2001) Chemical and Enzymatic Synthesis of DNA Fragments Containing 5-(B-D-Glucopyranosyloxymethyl)-2'-deoxycytidine—a Modified Nucleoside in T4 Phage DNA. European Journal of Organic Chemistry, 2001(11):2075-2082.*
Berkner et al. (1977) EcoRI Cleavage and Methylation of DNAs Containing Modified Pyrimidines in the Recognition Sequence. The Journal of Biological Chemistry, 252(10):3185-3193.*
Khulan et al. (2006) Comparative isoschizomer profiling of cytosine methylation: The HELP assay. Genome Research, 16:1046-1055.*
Bair et al. (2007) A Type IV Modification Dependent Restriction Nuclease that Targets Glucosylated Hydroxymethyl Cytosine Modified DNAs. Journal of Molecular Biology, 366:768-778.*
Weber et al. (2007) Distribution, silencing potential and evolutionary impact of promoter DNA methylation in the human genome. Nature Genetics, 39(4):457-466.*
Roberts et al. (2007) REBASE-enzymes and genes for DNA restriction and modification. Nucleic Acids Research, 35:D269-D270.*
Tahiliani, M., et al, Science, 324 (5929), 930-935 (2009).
Kriaucionis, S., et al, Science, 324 (5929), 929-930 (2009).
International Search Report and Wiritten Opinion, Australian Patent Office, Oct. 15, 2010.
Shendure and Ji, Nature Biotechnology 26: 1135-1145 (2008).
Janosi et al. J. Mol. Biol. 242: 45-61 (1994).
Bair, et al. J. Mol. Biol. 366: 768-778 (2007).
Cliffe et al. Nucleic Acids Res. 37(5): 1452-1462 (2009).
Szwagierczak et al. NAR-39, 12, 5149-5156_2011.

(Continued)

*Primary Examiner* — Juliet Switzer
*Assistant Examiner* — Neil P Hammell
(74) *Attorney, Agent, or Firm* — New England Biolabs, Inc; Harriet M. Strimpel

(57) ABSTRACT

Methods and compositions are described for detecting hydroxymethylated nucleotides (hmNs) in a polynucleotide preparation with a view to mapping the location of hmNs in a genome, quantifying the occurrence of hmNs at selected loci and correlating the occurrence of hmNs with gene expression and phenotypic traits. Embodiments describe the use of modifying enzymes together with site-specific endonucleases to detect the hmNs.

14 Claims, 22 Drawing Sheets

(56) References Cited

OTHER PUBLICATIONS

Szwagierczak, et al. NAR 38(19) e181 (2010).
Borst et al. Annu Rev Microbiol. 62:235-51 (2008).
Gommers-Ampt et al. Cell 75: 1129-1136 (1993).
Huang et al. Nucleic Acids Res. 10: 1579-1591 (1982).
Bair, et al., "Exclusion of Glucosyl-Hydroxymethylcytosine DNA Containing Bacteriophages", J Mol Biol., 366(3): 779-789, 2007.

* cited by examiner

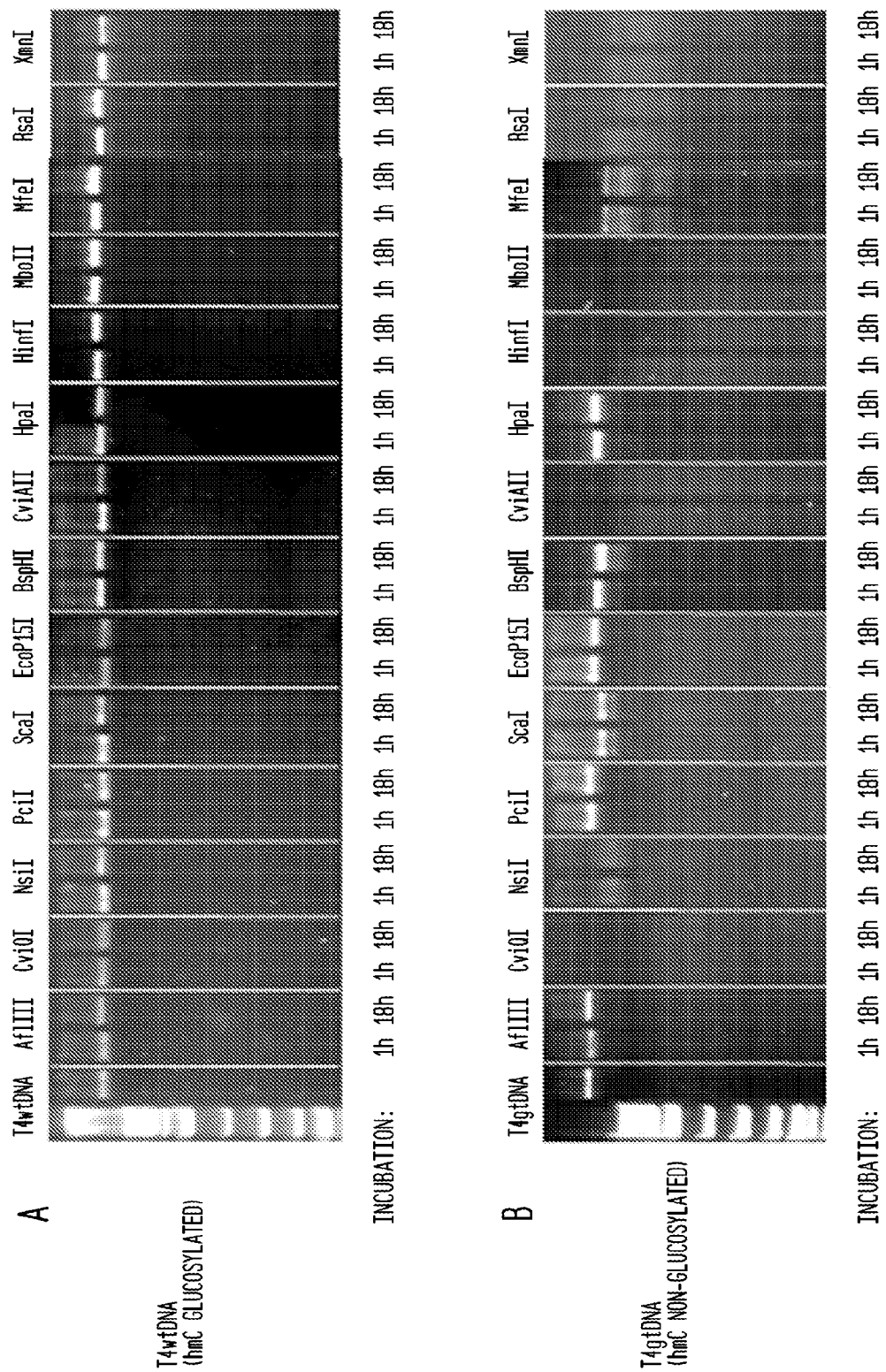

(1)

5'-FAM-ACACCCATCACATTTACAC  (SEQ ID NO:19)
3'-TGTGGGTAGTGTAAATGTGGCCTATTCTCAACTTACATCTCAACC-FAM-5'  (SEQ ID NO:20)

(2)

5'-FAM-ACACCCATCACATTTACACCGGATAAGAGTTGAATGTAGAGTTGG-3'  (SEQ ID NO:21)
3'-TGTGGGTAGTGTAAATGTGGCCTATTCTCAACTTACATCTCAACC-FAM-5'  (SEQ ID NO:22)

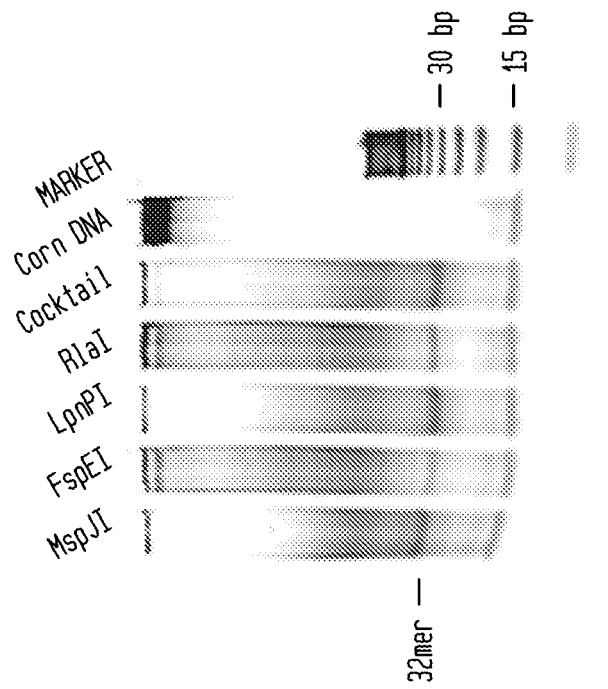
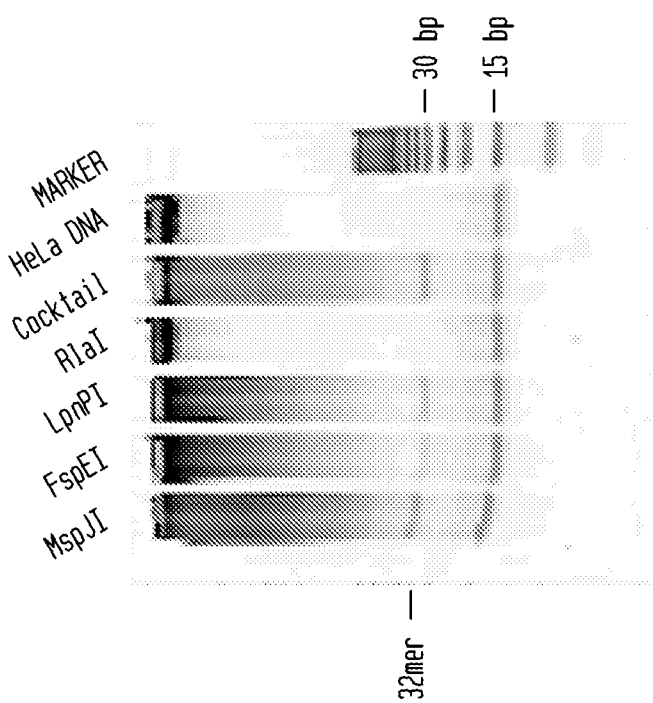
FIG. 6 (CONT)

FIG. 18
A
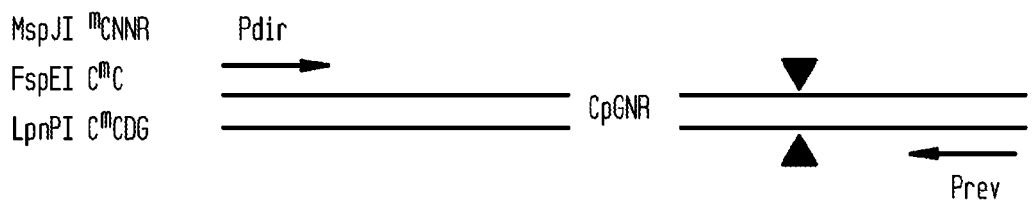
B
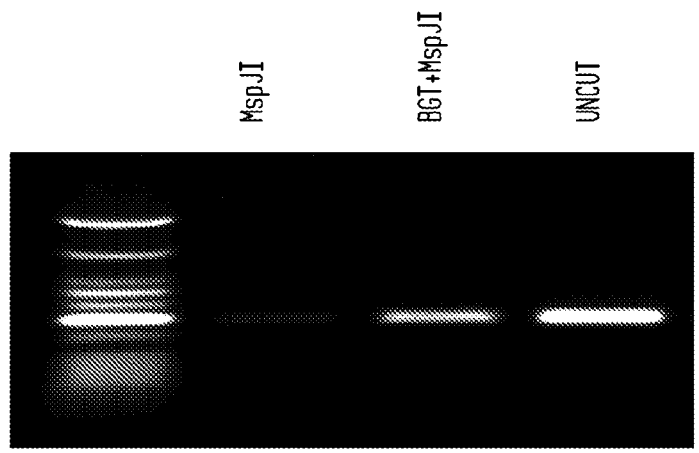
C
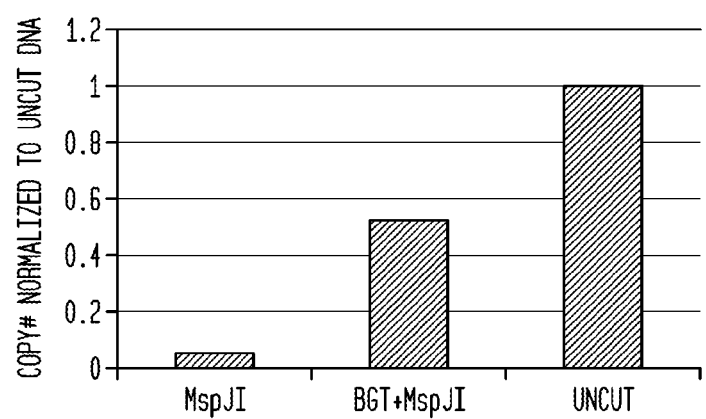

US 9,034,597 B2

DETECTION AND QUANTIFICATION OF HYDROXYMETHYLATED NUCLEOTIDES IN A POLYNUCLEOTIDE PREPARATION

CROSS REFERENCE

This application is a §371 application of international application number PCT/US2010/46632 filed on Aug. 25, 2010, which claims priority from U.S. provisional application No. 61/275,136 filed Aug. 25, 2009, 61/254,346 filed Oct. 23, 2009, 61/354,826 filed Jun. 15, 2010, and 61/370,037 filed Aug. 2, 2010, herein incorporated by reference.

BACKGROUND

After the reports by Kriaucionis et al. (*Science* 324:929-930 (2009)) and Tahiliani et al. (*Science* 324:930-935 (2009)) there has been a growing interest in detecting, locating and measuring hydroxymethylated nucleotides (hmNs), in particular, hydroxymethylated cytosines (hmCs), to better understand gene expression in eukaryotic cells, and in particular, mammalian cells. Unfortunately, sodium bisulfite sequencing does not differentiate between hmNs and methylated nucleotides (mNs). MspI which is an enzyme that is sometimes used along with HpaII to identify methylated cytosine (mC) also does not discriminate between hydroxymethylated and methylated DNA. Binding proteins used to immobilize fragments of DNA on an affinity substrate where the fragments contain a modified nucleotide do not differentiate between one or multiple modified nucleotides on the DNA fragment. This has meant that not only is it unknown where in the genome hmNs occur, but also how their presence and distribution varies in a genome according to the changing environment of the cell or the stage of a cell in differentiation.

SUMMARY

In an embodiment of the invention, a method is provided for detecting an hmN in a polynucleotide preparation. The method requires that the hmN in the polynucleotide preparation is modified and the polynucleotide preparation cleaved with a site-specific endonuclease, the site-specific endonuclease being capable of cleaving a polynucleotide that has a specific recognition site containing one or more mNs or hmNs but not a modified hmN (mhmN). Accordingly, a polynucleotide in the polynucleotide preparation may be detected if it contains an hmN in the recognition sequence because when the hmN is modified, it is not cleaved whereas when the hmN is unmodified, the polynucleotide will be cleaved. Hence, detection of the hmN generally results from detection of uncleaved and additionally from cleaved polynucleotides in the polynucleotide preparation under selected conditions.

In embodiments of the invention, the hmN may preferably be hmC. In some embodiments, the mhmN refers to a glucosylated hmN (ghmN) or more particularly, a glucosylated hmC (ghmC).

"a" composition as used here is intended to mean "one or more" of the composition.

The "polynucleotide preparation" refers to a single polynucleotide or a plurality of polynucleotides in solution or immobilized on a matrix preferably in vitro. The polynucleotide preparation may contain a single copy or multiple copies of a single sequence or may contain a mixture of polynucleotides with varying sequences. The polynucleotides may be derived from a genomic DNA where the genomic DNA may be a mammalian or other eukaryotic genome or a prokaryotic genome but does not include bacterial virus DNA. The polynucleotides in the preparation may include additional defined sequences in the form of double- or single-stranded oligonucleotides hybridized to one or both termini. These oligonucleotides may be synthetic and include adapters or primers or labels. The polynucleotides may be synthetic oligonucleotides.

The site-specific endonucleases used in embodiments of the method described above may additionally have features that include recognizing a sequence containing the hmN or a sequence preference containing the hmN (referred to as a recognition site) or the hmN only in a polynucleotide, and cleaving at a fixed distance from the specific nucleotide where the specific nucleotide. The polynucleotide may be single- or double-stranded DNA or RNA or a hybrid DNA/RNA. Preferentially, the polynucleotide is double-stranded DNA. In particular embodiments, the specific nucleotide is a cytosine (C). For example, site-specific endonucleases that recognize DNA containing one cytosine in the specific recognition sequence and cleave the DNA even when the cytosine is methylated or hydroxylated but not when the hmC is modified are exemplified in Table 1. Examples of site-specific endonucleases that recognize DNA at specific recognition sequences containing more than one cytosine and cleave the DNA if only one of the plurality of cytosines at a specific location in the recognition sequence is methylated or hydroxymethylated but not modified hydroxymethylated are provided in Table 2.

Site-specific endonucleases that recognize a single mN or hmN, but do not cleave mhmNs and may additionally have a preference for certain nucleotides in the vicinity of the mN or hmN are exemplified by the MspJI family and mutants thereof. Sequence preferences around the mN or hmN may provide enhanced cleavage efficiency for members of the MspJI family as exemplified in Table 3. Preferentially, modification refers to glucosylation of the hmN, in particular, glucosylation of hmC.

In embodiments of the invention, it may be desirable to utilize a plurality of site-specific endonucleases having different recognition sequence preferences to create a comprehensive genomic map of hmNs (a hydroxymethylome) or for other purposes. The plurality of site-specific endonucleases may include not only those types of enzymes exemplified in Tables 1 to 3, but also Type IV restriction endonucleases such as GmrSD which can cleave DNA containing a ghmC in both alpha and beta configurations in the recognition sequence and also the PvuRts1I family of enzymes which can cleave modified (e.g. glucosylated) hmNs and hmNs.

In an embodiment of the invention, the method described above may additionally utilize adapters in order to detect hmNs. The adapters may be ligated to the ends of polynucleotides either before or after the polynucleotide preparation is cleaved and either before or after modification of the hmN. The cleavage step may occur before and/or after modification. The adaptor-ligated polynucleotides may be used for amplification or sequencing or both. The same or different adapters may be present on the ends of the polynucleotide during the detection of hydroxymethylation, for example, prior to amplification and/or sequencing as illustrated in FIGS. 8 and 9. Detection of hmNs may alternatively be achieved, for example, by using nanopore technology (see, for example, Oxford Nanopore, Oxford, U.K.) or hybridization techniques.

In an embodiment of the invention, the method includes identifying a genome location for the one or more hmNs determined from detection of uncleaved modified polynucleotides resulting from methods described above. For example, the polynucleotide containing the hmN can be sequenced and the sequence of the polynucleotide matched to a genome sequence using standard bioinformatic mapping techniques known in the art. Preferably, the sequence of the polynucleotide is matched to a reference genome from the same species of organism from which the polynucleotide is derived. In this way, a hydroxymethylome may be created in which hmNs are mapped to the genome throughout its length. More particularly, a genome locus is defined by a sequence containing a single or a plurality of hmN. The genome locus may be used as a reference or as a target where it may also be referred to as a predetermined locus in the genome.

In an embodiment of the invention, the occurrence of an hmN at a genomic locus can be determined de novo or matched to a predetermined genomic locus using embodiments of the methods described herein for detecting hmN in a polynucleotide preparation derived from a cell, a tissue or an organism. Determination of the sequence context surrounding an hmN can be evaluated by a variety of methods including sequencing, hybridization and end-point PCR.

In additional embodiments, a method is provided for quantifying the occurrence of an hmN at a genomic locus by analyzing a polynucleotide preparation from a plurality of cells, a tissue or an organism using a quantification method known in the art such as qPCR, end-point PCR, bead-separation and use of labeled tags such as fluorescent tags or biotin-labeled tags. Uses of these techniques are exemplified in FIGS. 3A-3B, 13-15, 16A and 16B, 17 and 18A-18C and corresponding examples. As illustrated in the figures, the amount of hydroxymethylation at a particular locus can be compared between different polynucleotide preparations from different cells, tissues, or organisms or the same cells, tissues or organisms at different stages of development or exposed to different environments.

In an embodiment of the invention, a method is provided for detecting an hmN in a polynucleotide preparation and comparing the occurrence of the hydroxymethylation in a first polynucleotide preparation with the occurrence of an hmN in a second polynucleotide preparation. Another embodiment of the invention, additionally comprises correlating the occurrence of the hmN at an identified locus, which may be predetermined, with a phenotype.

Embodiments of the method may be used to detect an hmN in a polynucleotide preparation so as to compare polynucleotides from a single tissue from a single host or a plurality of polynucleotides from a plurality of tissue samples from a single host with a reference genome or locus, or to compare a plurality of polynucleotides from a single tissue from a plurality of hosts or a plurality of polynucleotides from a plurality of tissues from a plurality of hosts with each other.

In an embodiment of the invention, the method of detecting an hmN in a polynucleotide preparation further includes recording in a computer-readable form detection data indicative of the occurrence of an hmN in a polynucleotide preparation. The detection data may be binary in the form of presence or absence of the hydroxymethylation site. The detection data may be a product of the calculations provided in the examples (see for example, Examples 15 and 17). The detection data may include an address corresponding to the characteristics of the polynucleotide fragment such as size, source, environmental context, age or developmental condition of the source as well as an identified genomic locus if available corresponding to the detection data for the polynucleotide preparation. The address may alternatively or additionally contain a code to identify the order in which data is inserted into a database and any weighting deemed applicable.

In an embodiment of the invention, a kit is provided for performing a method for detecting one or more hmNs in a polynucleotide preparation. The kit comprises: a glucosyltransferase and a site-specific endonuclease in a single container or in separate containers, the site-specific endonucleases being capable of cleaving a polynucleotide having a specific recognition site containing an mN or hmN, but not an mhmN; and instructions for use according to any of the embodiments described above. The kit may additionally include a ligase and an adapter.

In an embodiment of the invention, a computer program product is provided that includes: (a) a computer-readable storage medium; and (b) instructions stored on the computer-readable storage medium that when executed by a computer cause the computer to receive detection data for the polynucleotide preparation obtained according to the present method, and to perform at least one of: mapping the hmN detection data to a genome sequence; comparing the detection data of hmNs in the polynucleotide preparation with a reference polynucleotide; and identifying biological markers from the detection data.

In a further embodiment, the computer program product may further require instructions that when executed by the computer further cause the computer to identify in the database reference polynucleotides having substantially similar patterns of hydroxymethylation to that of the polynucleotide preparation.

A "reference" polynucleotide as used here refers to a polynucleotide optionally in a database with defined properties that provides a control for the polynucleotide preparation or polynucleotide being investigated for hydroxymethylation.

A "reference" genome includes a genome and/or hydroxymethylome where the hydroxymethylome is a genome on which an hmN has been mapped. The reference genome may be a species genome or a genome from a single source or single data set or from multiple data sets that have been assigned a reference status.

"Substantially similar" as used here refers to at least compositions or patterns or other items which, when compared, are not necessarily identical but share at least 50%, or as much as 60%, 70%, 80% or 90% of a quantified amount of a trait.

In an additional embodiment of the computer program product invention, the instructions when executed by the computer further cause the computer to search for a phenotype designation associated with the identified reference polynucleotide.

A "phenotype designation" refers to a coded description of a physical characteristic of the cell, tissue or organism from which the polynucleotide is derived which is correlated with gene expression and with the presence of an hmN. The phenotype being designated may be, for example, a gene expression product that would not otherwise occur, a change in a quantity of a gene expression product, a cascade effect that involves multiple gene products, a different response of a cell or tissue to a particular environment than might otherwise be expected, or a pathological condition.

It should be appreciated that the computer program product may be used for diagnostic tests in a clinic or agricultural station or for treatment of a patient either by monitoring an effect of a certain drug treatment on a patient or by prognosis or diagnosis of symptoms of the patient that would lead to an appropriate treatment of the presented medical condition.

BRIEF DESCRIPTION OF THE DRAWINGS

FIGS. 1A and 1B show the results of screening for restriction enzymes that discriminate between hmC and glucosylated hydroxymethylcytosine (ghmC).

FIG. 1A shows a genomic DNA substrate from wild type bacteriophage T4 (T4 wt), which is hydroxymethylated and glucosylated at every cytosine, and reacted with 14 restriction endonucleases. No cleavage of glucosylated DNA was observed.

FIG. 1B shows a genomic DNA substrate from T4 mutants defective in α-glucosyltransferase 57 (AGT) and β-glucosyltransferase 14 (BGT) (T4gt) which is not capable of glucosylation of hmC. Accordingly, hmC in the mutant T4 genome remains hydroxymethylated at every cytosine. The mutant T4 genome was reacted with the 14 endonucleases shown in FIG. 1A. Eight of these enzymes, CviQI, NsiI, CviAII, HinfI, MboII, MfeI, RsaI and XmnI, cleaved hmC DNA but not ghmC DNA.

FIG. 2A shows that duplex 1 contains a single hmC (large, bold C) residue within the sequence $C^{hm}CGG/GGCC$. Duplex 1 is formed as follows: (1) Anneal primer; and (2) Fill in using Klenow fragment and $d^{hm}CTP$, dATP, dTTP, dGTP.

FIG. 2B shows that Duplex 2 contains two hmC (large, bold C) residues on opposite strands of the recognition sequence $C^{hm}CGG/GG^{hm}CC$. Duplex 2 is formed as follows: (1) Anneal primer; (2) Fill in using Klenow fragment and $d^{hm}CTP$, dATP, dTTP, dGTP; (3) Excise deoxyuracils from duplex 1 with the USER™ enzyme (New England Biolabs, Inc., Ipswich Mass. (NEB)); (4) Anneal primer; and (5) Fill in using Klenow fragment and $d^{hm}CTP$, dATP, dTTP, dGTP.

FIG. 6A shows cleavage activity of the specified enzyme on pBR322 dcm$^+$ methylated plasmid DNA.

FIG. 6B shows cleavage activity of the specified enzyme on pBR322 dcm$^-$ (unmodified) plasmid DNA.

FIG. 6C shows cleavage activity of the specified enzyme on mutant T4gt (hydroxymethylated) genomic DNA, FIG. 6D shows cleavage activity of the specified enzyme on T4 wt (glucosylated) genomic DNA.

FIG. 6E shows cleavage of a Hela genome by different members of the MspJI family The 32 mer product is indicated as a band and the lower band (A) corresponds to the activator. A DNA ladder indicates the position of 30 bp and 15 bp.

FIG. 6F shows cleavage of a corn genome by different members of the MspJI family. The cleavage profile obtained from RlaI cleavage of mammalian DNA differs from the cleavage profile in plants. The 32 mer product is indicated as a band and the lower band (A) corresponds to the activator. A DNA ladder indicates the position of 30 bp and 15 bp.

Digestion by MspI is followed by treatment with Klenow fragment in the presence of dCTP, leaving termini with 5'C overhangs. These termini are substrates for ligation to duplex adapters with 5'G single base overhangs flanked by a GC base pair, thus recreating the CCGG site. Duplex adapters are denoted as BC#1 (Boxes marked A/B), BC#2 (Boxes marked C/D), and BC#3 (Boxes marked E/F). Sequences of these three duplexes are given in Table 4. After ligation of BC#1 adapters, samples were treated with BGT and UDP-Glu to glucosylate the hmC residues. These ligated samples were then digested with MspI (a). Repetition of these cycles, using different duplex adapters in each cycle, resulted in fragments with terminal adapters determined by the modification status of the central CG dinucleotide (b) and (c). In the final reaction (c), samples were cut with HpaII rather than MspI prior to ligation of the final adapter duplex BC#3. Reading the sequence of the adapter and adjacent sequence of all three pathways revealed the modification status present in the genomic DNA sample at that CCGG site, along with enough flanking sequence information to assign a genomic location to the CCGG site.

Figure 9:
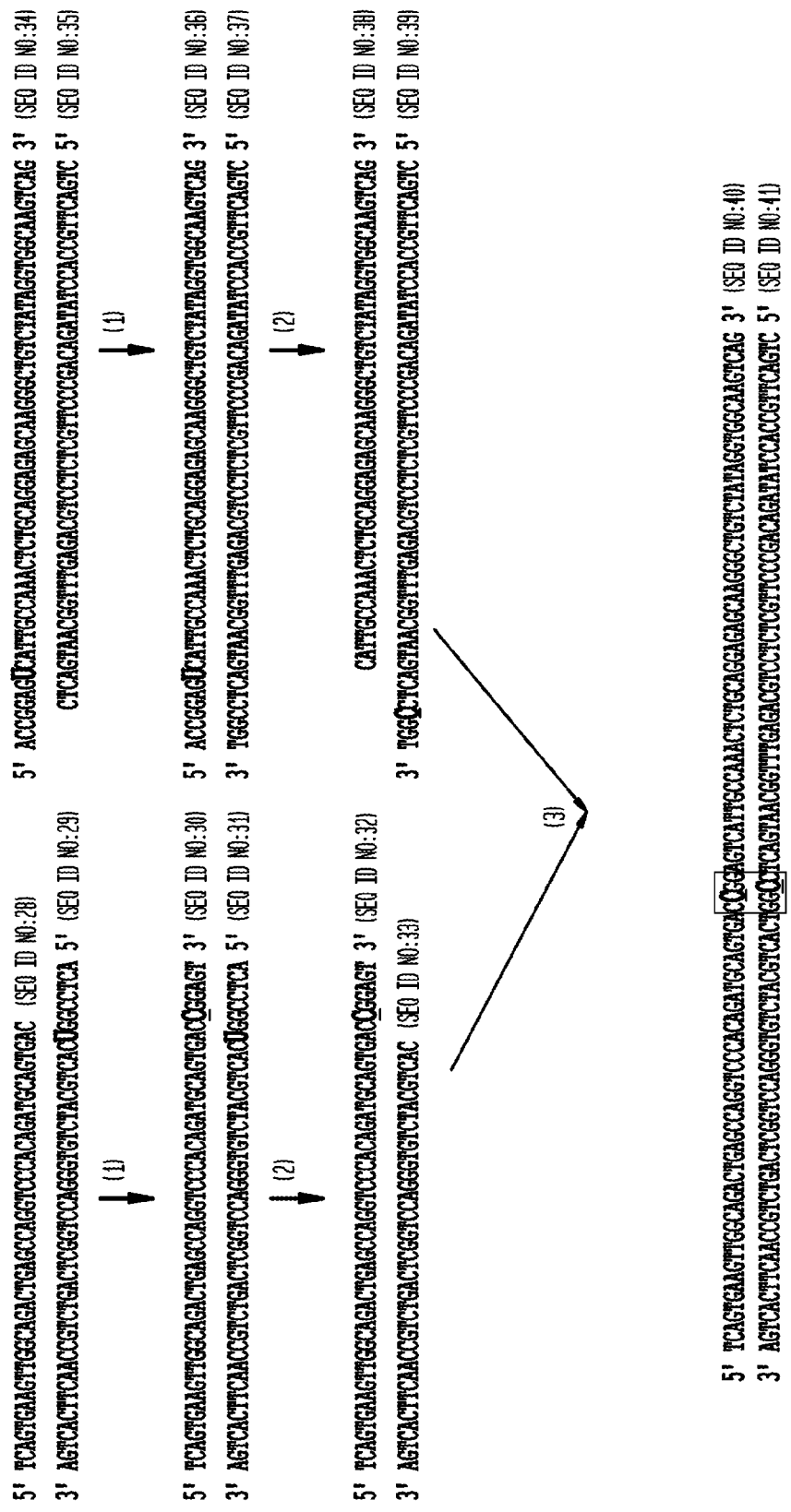

FIG. 9 shows a schematic of the design and synthesis of double-stranded substrates in which the central cytosine residue in the sequence ACCGGA (underlined) is C, mC, or hmC. Creation of the substrate include the steps of: (1) fill-in repair of termini of Oligo I using Klenow fragment exo+ in the presence of dTTP, dGTP, dATP, and $d^mCTP$ or $d^{hm}CTP$ (ds Oligo I), or dCTP (Oligo II); (2) cleavage of both duplexes with USER™ to create overhangs; and (3) ligation of Oligo I and II to form the substrate using T4 DNA ligase. This results in a substrate with C, mC, or hmC at the underlined position. The substrate was reacted with MspI or BsaWI to test the sensitivity of MspI and BsaWI to methylation and hydroxymethylation of the central C in the sequence $AC^{hm}CGGT/AC^{hm}CGGT$.

Figure 10:
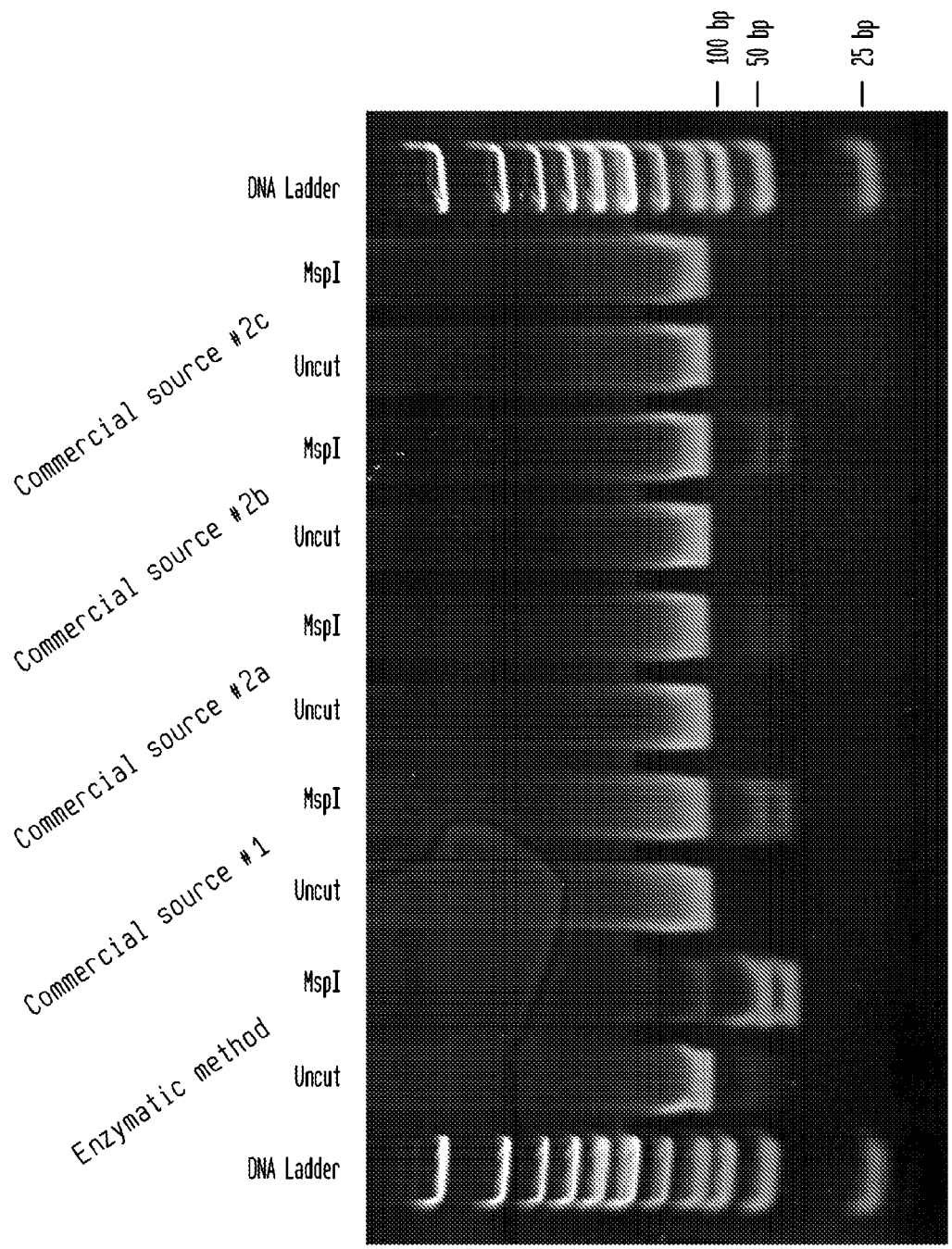

FIG. 10 shows the results of using oligonucleotide substrates from varying sources. MspI successfully cleaved an oligonucleotide prepared according to FIG. 9 that contained $C^{hm}CGG$. The commercial oligonucleotides that were tested, which allegedly contained $C^{hm}CGG$, were not cleaved by MspI.

Figure 11:
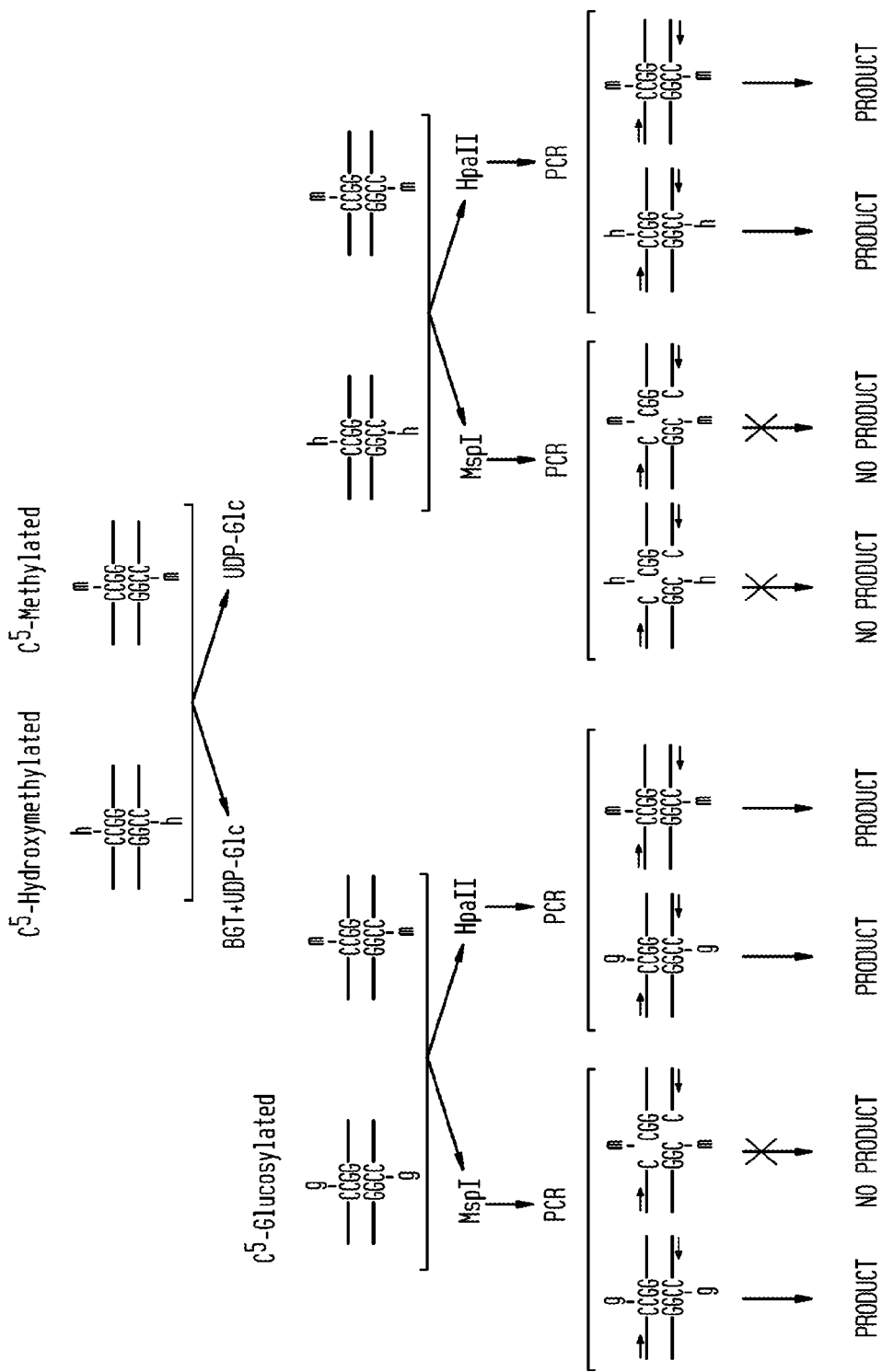

FIG. 11 shows a hmC detection procedure for a locus. First, the DNA of interest was treated with BGT and UDP-Glc. Control samples were incubated with UDP-Glc only and therefore lack modification. BGT transferred glucose from UDP-Glc onto hmC (marked as "g"). MspI cut DNA containing hmC or mC, but did not cut DNA containing ghmC; in contrast, HpaII cleavage is blocked by both ghmC and hmC. If the CpG site of interest was hydroxymethylated, a PCR amplification product resulted after BGT-treatment and MspI-digestion.

Figure 12:
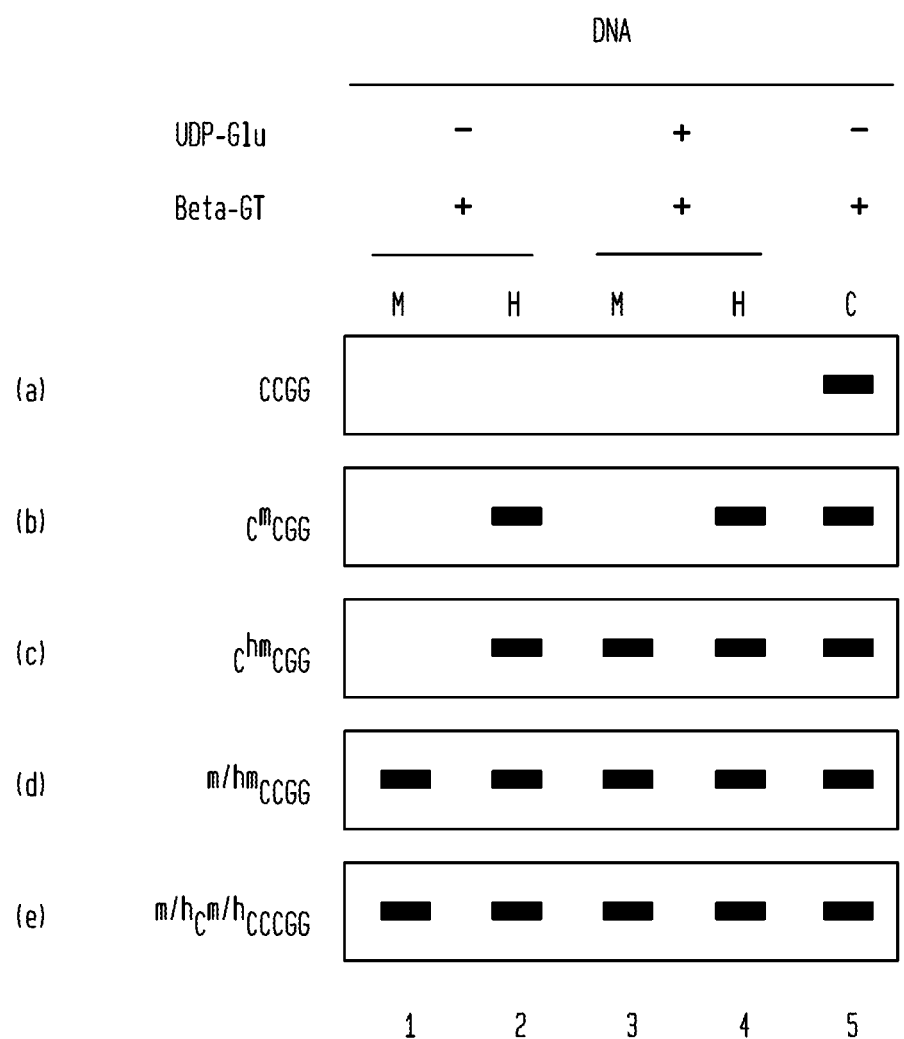

FIG. 12 shows the expected patterns of PCR products from various modified substrates after treatment with MspI or HpaII.

The cartoon illustrates expected PCR products (a) to (e) using a primer set that flanks a single CCGG site, the recognition site for MspI and for HpaII. PCR products were produced when the site was uncut. Conversely, no PCR product was observed when the CCGG site was completely digested.

The DNA samples represented contain mC or hmC at indicated positions. A single strand is indicated here since in each instance modification of a single strand produced the same end point PCR result as complete modification. Plus (+) and minus (−) indicate treatment of the DNA with UDP-Glc and/or BGT. Samples treated with both UDP-Glc and BGT had ghmC in place of hmC. Lanes marked M and H show digestion with MspI and HpaII, respectively, prior to PCR.

A control sample (C, lane 5) shows the result of PCR amplification of DNA samples incubated with BGT and UDP-Glc substrate, but not digested with either enzyme.

Figure 13:
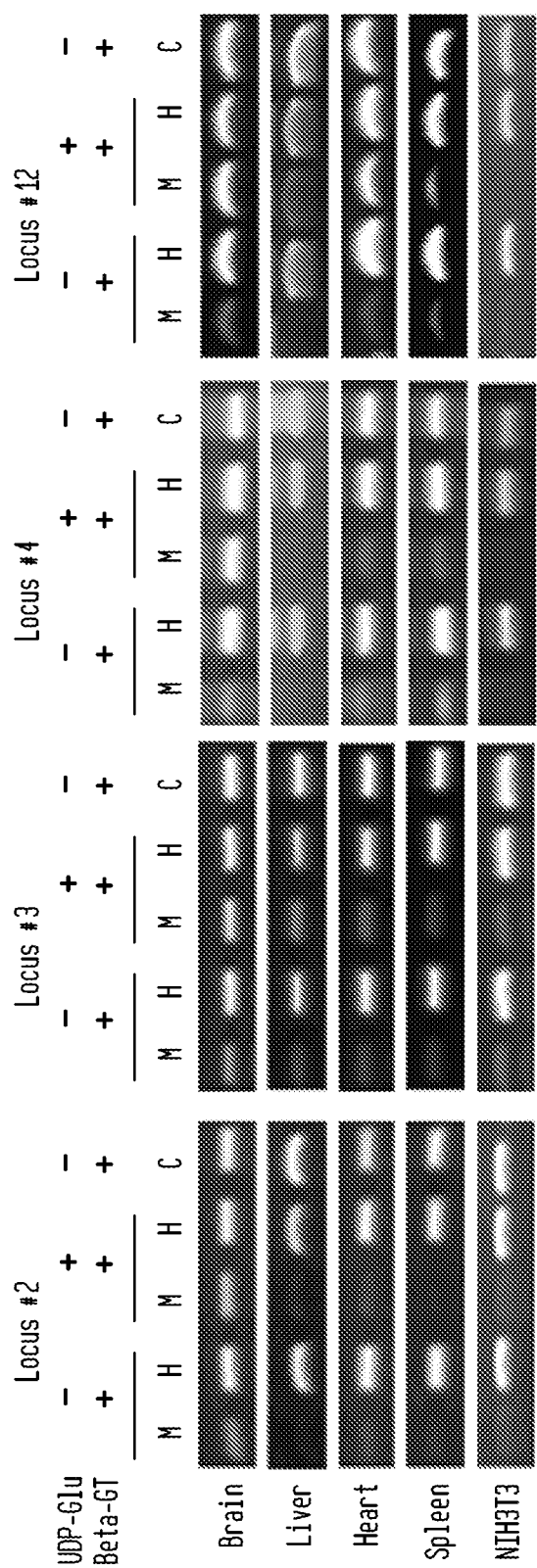

FIG. 13 shows variation in hmC content of DNA depending on tissue type and locus within the tissue. Locus-specific endpoint PCR was used to interrogate and detect hmC at selected CCGG sites in genomic DNA isolated from natural sources. Treatment with UDP-Glc and/or BGT are denoted by a + sign. Samples in which hmC was converted to ghmC were resistant to MspI cleavage at $C^{hm}CGG$ sites. Lanes marked with M and H show samples digested with MspI and HpaII, respectively, prior to PCR amplification. Samples in lanes marked by C were not digested prior to PCR amplification.

Figure 14:
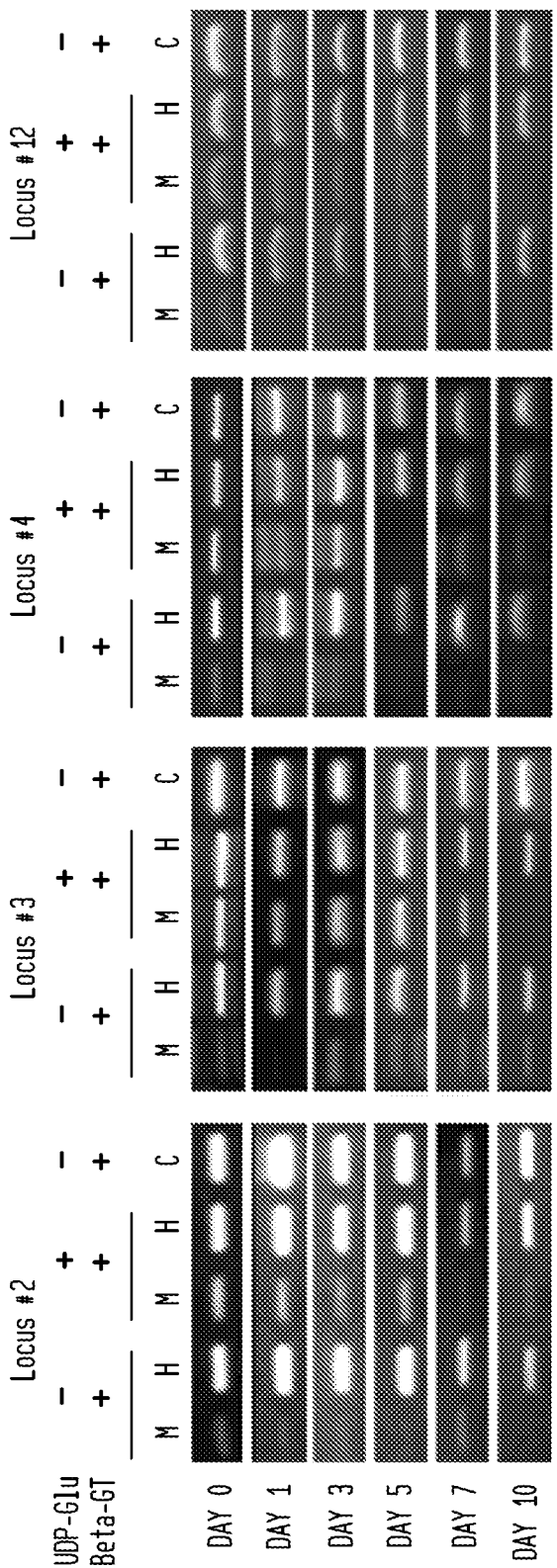

FIG. 14 shows that amounts of hmC vary during ES14 cell development in a locus-dependent fashion. The occurrence of hmC during embryonic stem differentiation to embryoid bodies was interrogated at four loci as described in Example 12, and presented in the same format as FIG. 13. Genomic DNA samples were prepared from ES14 cells at intervals after induction of differentiation, with intervals indicated to the left of each row (0, 1, 3, 5, 7, and 10 days).

Figure 15:
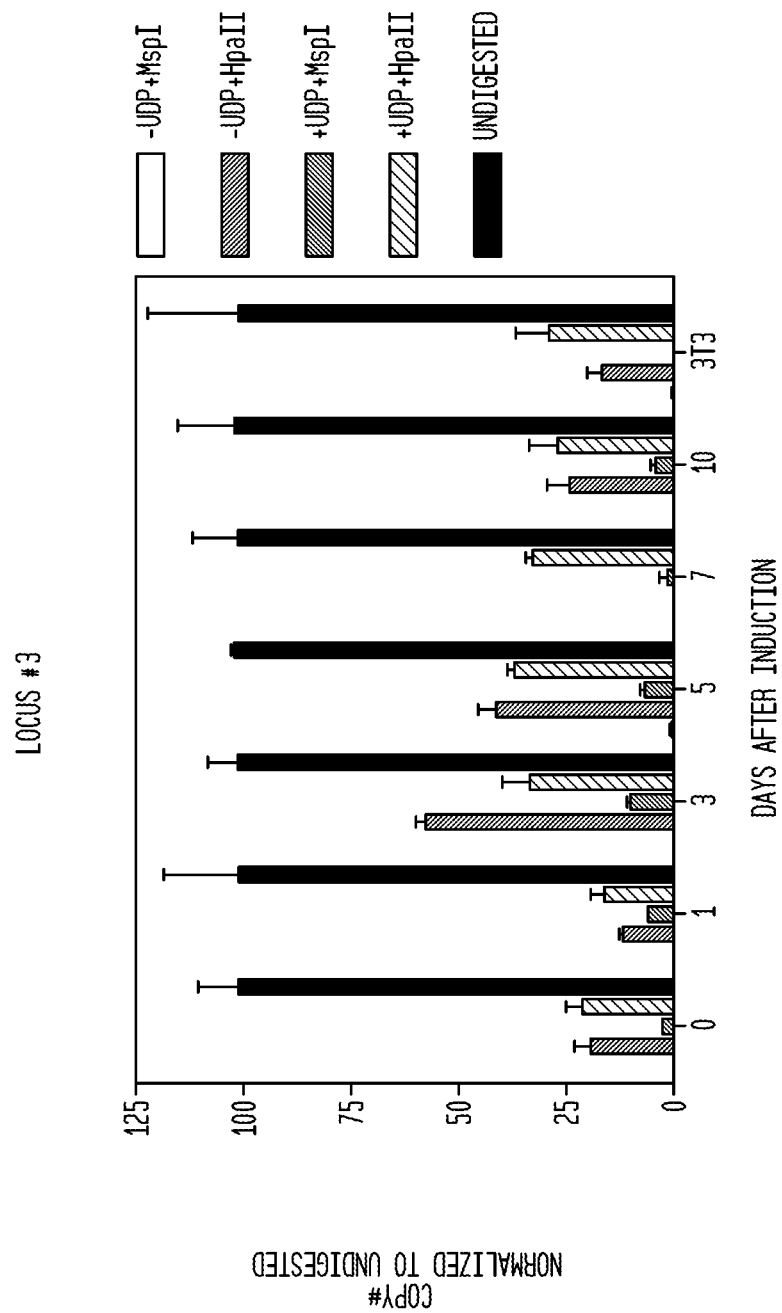

FIG. 15 shows how mC and hmC variation can be quantified during differentiation. Analysis described in Example 12 and FIG. 14 was extended by performing qPCR analysis of locus #3 (see Example 14). All samples were treated with BGT. Selected samples additionally included the substrate UDP-Glc (+UDP). Other samples did not include UDP-Glc (−UDP). Only samples (+UDP) resulted in conversion of hmC residues to ghmC. Samples were then incubated with buffer alone (undigested), MspI, or HpaII to digest susceptible sites. Subsequent PCR analysis quantified the amount of undigested sample to determine the extent of mC and hmC present in the samples. Labels on the abscissa indicate the time (days) elapsed from induction of differentiation. 3T3 (terminally differentiated NIH3T3 cells) are a negative control for hmC.

Figure 16:
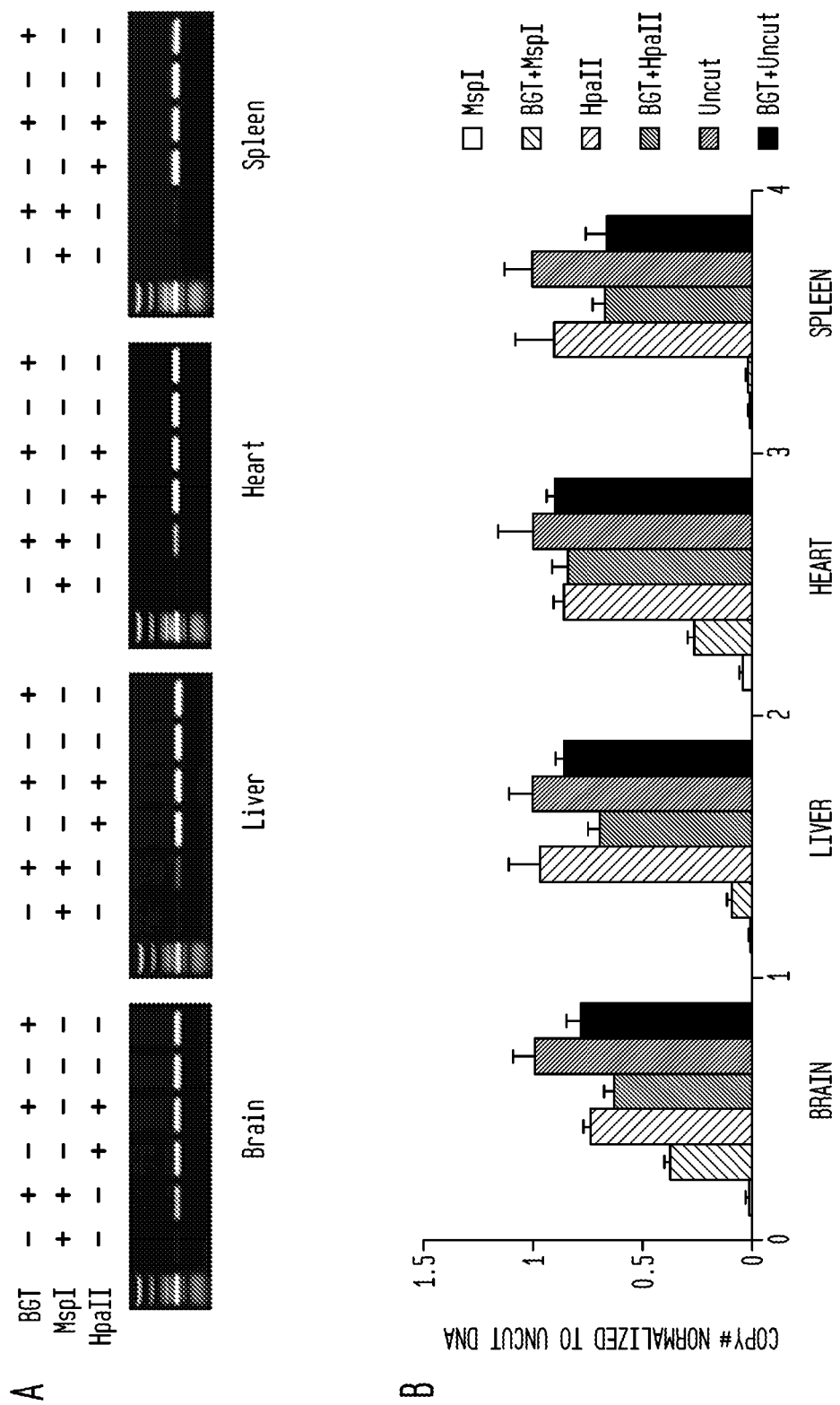

FIGS. 16A and 16B show a quantitative analysis of hmC in different mouse NIH 3T3 tissue samples.

FIG. 16A shows a gel analysis of amplified products from endpoint PCR after enzyme digestion of samples treated as indicated above each lane for brain, liver, heart and spleen in that order.

FIG. 16B shows real time PCR (qPCR). Brain, liver, heart and spleen tissues were analyzed. For comparative purposes, real time PCR data were normalized to uncut DNA. A standard curve was used to determine copy number. The samples could be normalized by dividing the copy number of samples Nos. 1-6 by the copy number of the control undigested sample (No. 5). Samples are from left to right: brain, liver, heart, spleen. Height of bars represent the copy number normalized to uncut DNA. Samples: (1) MspI, (2) BGT+MspI, (3) HpaII, (4) BGT+HpaII, (5) uncut, (6) BGT+uncut.

Figure 17:
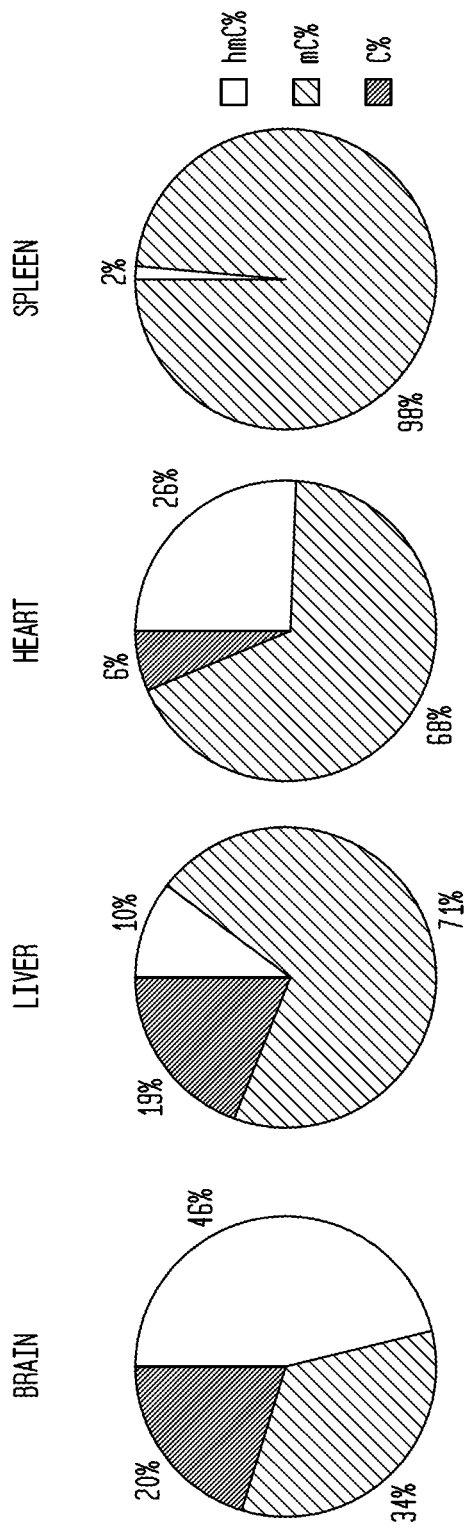

FIG. 17 provides a determination at a single locus of the % hmC:% mC:% C using BGT, MspI, and HpaII derived from qPCR data shown in FIG. 16B and represented here in pie charts (see also corresponding Table 8)

FIGS. 18A-18C show how the presence of a hmN in a DNA can be rapidly and easily detected using a modifying enzyme (BGT) and a site-specific endonuclease.

FIG. 18A shows a hypothetical CpG, which can be cleaved by the examples of enzymes on the left side (MspJI $^mCNNR$, FspEI $C^mC$ and LpnPI $C^mCDG$).

FIG. 18B shows a simulated gel-based result from enzyme cleavage of modified and unmodified DNA.

FIG. 18C shows a graphical representation of amounts of each lane in the gel, which provides the instrant determination of the presence of a hmN.

Figure 19:
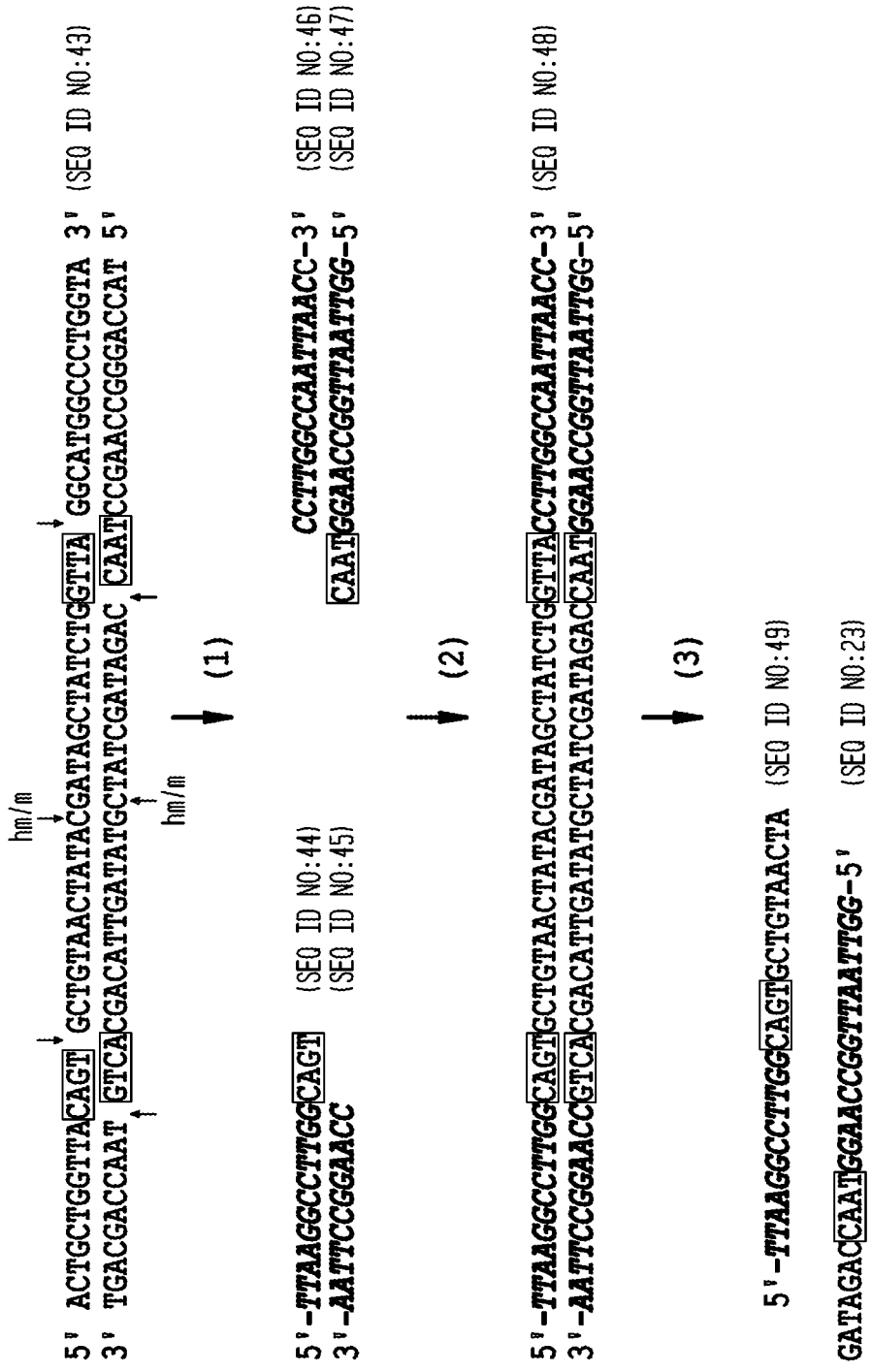

FIG. 19 shows a DNA that is analyzed for the presence of a hmN using adapters and primers to detect the hmC/mC nucleotides. (1) DNA is cleaved with MspJI (arrow indicates cleavage sites) resulting in an MspJI fragment with 4-base overhangs (in box); (2) the fragment is ligated with two different double-stranded adapters (bold), one on each end; and (3) the product of ligation is denatured using the interrogating primers to test for the presence of each strand individually.

Figure 20:
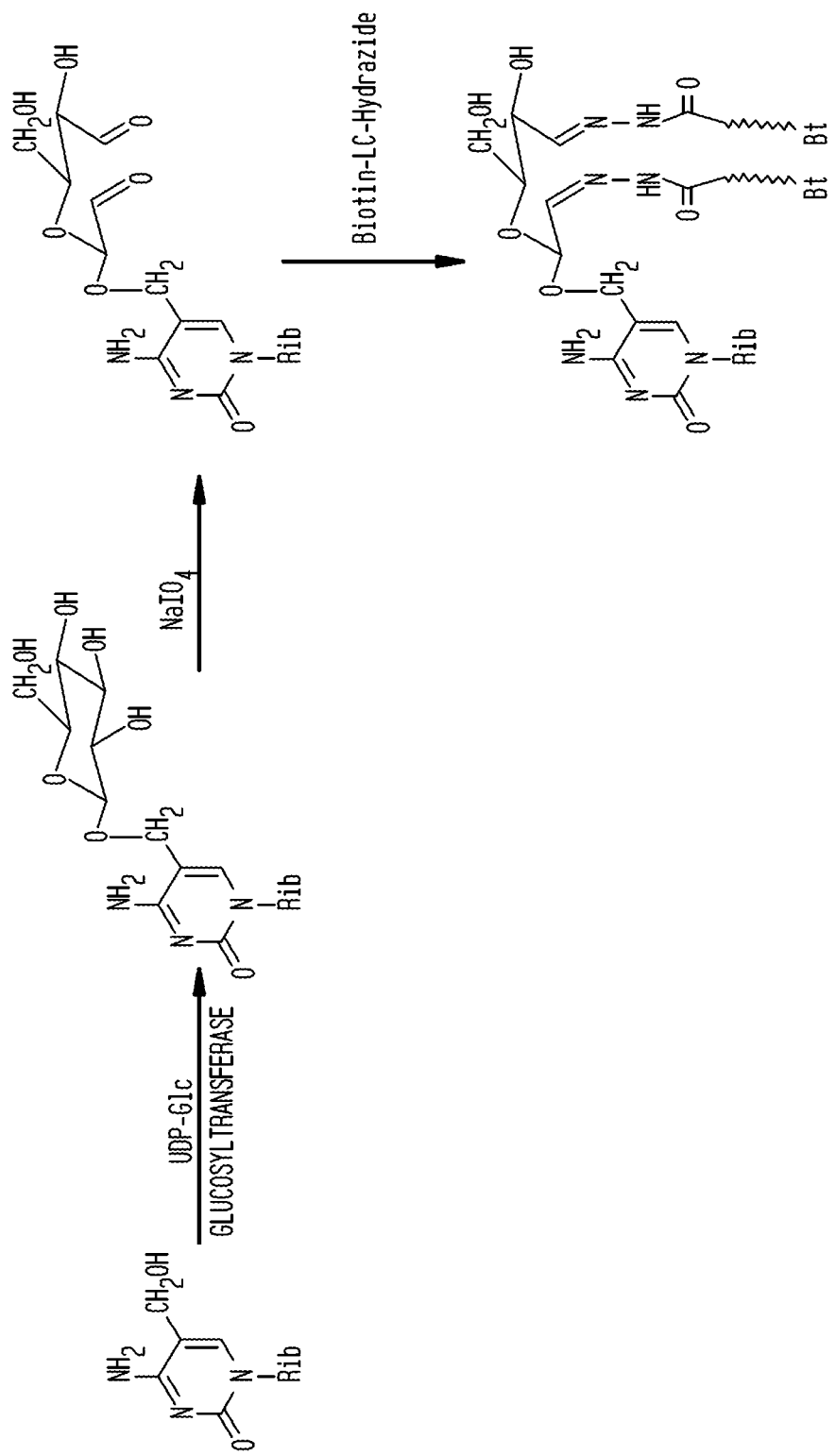

FIG. 20 shows direct chemical detection of ghmC. BGT transfers glucose from UDP-Glc to hmC in double-stranded DNA. Sodium periodate, followed by reaction with a labelled hydrazide, allows addition of a detection label (biotin shown) to the residues that originally were hmC.

DETAILED DESCRIPTION OF THE EMBODIMENTS

Identification and quantification of the occurrence of a hmN in DNA has been achieved here by using reagents that differentially act on a modified hydroxymethylated nucleotide (mhmN) and/or hmN, compared with an mN and/or nucleotide (N).

Methods are provided herein to detect hydroxymethylation in a genome (see for example, Examples 7, 8 and 10) and to identify specific loci of hydroxymethylated nucleotides in a genome (see for example, Examples 9 and 11). Once specific locations of hydroxymethylation were identified, different tissues in an organism were examined to determine intertissue variability at a particular locus (see for example, Example 12). In addition, changes in hydroxymethylation were detected at specific loci during development of the organism (see for example, Example 13). Changes in hydroxymethylation can also be measured to determine disease conditions (see for example, Examples 15, 17 and 19).

Comparisons of hydroxymethylation patterns throughout the genome and at specific loci provide the basis for a growing database that can provide useful biomarkers for prognosis, diagnosis and monitoring of development, health and disease of an organism.

Modified hmNs and Reagents for Causing Modification

The term "modification" here and in the claims refers to a chemical group or biological molecule that is reacted with a hydroxyl group on a nucleotide in a DNA to become attached via a covalent bond.

Modification can be achieved by chemical or enzymatic means. In nature, certain bacterial viruses have modified hydroxymethylated cytosines (mhmCs) that result from the addition of glucose to the 5 position of cytosine via a glucosyltransferase to form 5-hmC.

Modification of the hmN in a DNA of interest results in a mhmN. For example, transferring a glucose molecule onto a hmN in a target DNA forms a glucosylated hmN (ghmN) such as ghmC. In embodiments of the invention, the hydroxymethylated DNA has a hydroxymethyl group on the C5 position of cytosine. In other embodiments, hydroxymethylation may occur on the N4 position of the cytosine, on the C5 position of thymine or on the N6 position of adenine. The methods described herein are broadly applicable to differentiating any mN or hmN at any position that additionally may be modified as described above. Selective modification of hmN in a DNA may be achieved enzymatically. For example, a sugar molecule such as glucose may be added to an hmN by reacting the DNA with a sugar transferase such as a glucosyltransferase. In the examples, a glucose is added to hmC using recombinant BGT. It was found that AGT works well when used in place of BGT; hence, wherever the use of BGT is described in the text and the examples, it may be substituted by AGT. Moreover, glucosyltransferases from phages T2 and T6 may be substituted for phage T4gt.

The mhmC is subsequently discriminated from mC and C in a cleavage reaction that would not otherwise have discriminated between hmC and mC. An additional example of an enzyme that modifies hmN is a glucosidase isolated from Trypanosomes that glucosylates hydroxymethyluracil (hmU) (Borst et al. *Annu Rev Microbiol.* 62:235-51 (2008)), Selective modification of hmN may be achieved chemically, for example, by binding a non-enzyme reagent to an hmN that blocks site-specific endonuclease cleavage, which would otherwise occur. Such chemical reagents may be used exclusively or in conjunction with additional molecules that label the hmN so that DNA containing hmN can be visualized or separated by standard separation techniques from DNA not containing modified hmN. Examples of non-enzyme reagents include antibodies, aptamers, protein labels such as biotin, histidine (His), glutathione-S-transferase (GST), chitin-binding domain or maltose-binding domain, chemiluminescent or fluorescent labels. Alternatively, selective chemical modification of hmN could be employed. This addition could by itself block site-specific endonuclease cleavage, or could bind additional non-enzyme reagents, such as those just described, to either block cleavage, allow visualization, or enable separation.

The modification of hmN results in altered cleavage patterns with a variety of different classes of enzymes. This provides an opportunity for exquisite resolution of individual or clustered hmN in a genome resulting from the varying specificities of the enzymes utilized as well as comprehensive mapping. Additional advantages include visualization of hmN molecules in the DNA of interest using chemical or protein tags, markers or binding moieties.

Enzyme Reagents for Detecting and Quantifying hmNs in a Biological Sample

Embodiments of the invention include the use of enzyme reagents that selectively act, or fail to act, on hmNs or mhmNs in contrast to Ns or mNs. Such enzyme reagents may be used in conjunction with additional reagents that either amplify the signal resulting from discrimination of hmN or substituted hmN or serve as markers to detect the product of the reaction. In an embodiment of the invention, the enzyme reagents are site-specific endonucleases.

Site-specific endonucleases suitable for use herein include endonucleases that recognize or ignore for purposes of cleavage either a specific nucleotide in a DNA that is hydroxymethylated or methylated or alternatively, one that is glucosylated, but not both. These site-specific endonuclease may cleave the DNA within the recognition site or at a distance from the recognition site on one side or both sides of the specific nucleotide preferably on the strand in the duplex that contains the specific nucleotide.

Site-specific endonuclease suitable for use herein can differentiate mhmNs from hmNs or mNs with respect to their ability to cleave the DNA. For example, mhmNs may be differentiated from hmNs because the site-specific endonuclease does not cleave mhmN or alternatively only cleave hmN or mhmN. It is envisaged that a plurality of site-specific endonucleases may be used to detect hmNs in a polynucleotide preparation where for example the polynucleotide is a genome. Site-specific endonucleases that recognize specific nucleotides in different sequence contexts can provide improved coverage of a hydroxymethylome for mapping purposes.

Examples of enzyme reagents for detecting and quantifying hmN include enzymes that differentially act on a mhmC and/or hmC, compared with an mC and/or C. These include the following:

(a) Enzymes that cleave DNA at a specific recognition sequence and have a cleavage specificity which is insensitive to the occurrence of hmC or mC at a specific site(s) in the recognition sequence, but whose cleavage is blocked when hmC is selectively modified (see for example Tables 1 and 2);

(b) Endonucleases that cleave within the recognition sequences and recognize sites containing a methyladenine, mC or hmC such as predicted for BisI, GlaI, GluI, MalI and PcsI; and GmrSD and related endonucleases that specifically cleave ghmC (Blair, et al. *J. Mol. Biol.* 366: 768-778 (2007))

(c) MspJI-related endonucleases and mutants thereof, where MspJI-related endonucleases cleave at a site distant from a recognition sequence containing an mN and/or hmN, where members of this family of enzymes have cleavage specificity for sequences that contain hmC or mC, but not C, and where cleavage is blocked when hmC is selectively modified (see, for example, Zheng et al. WO 2010/075375); and (d) PvuRts1I family which recognizes ghmC and hmC in DNA (U.S. Provisional Application No. 61/296,630 filed Jan. 20, 2010 and Janosi et al. *J. Mol. Biol.* 242: 45-61 (1994)) and cleave the DNA at an approximately fixed distance from that base.

(e) Type IV restriction endonucleases that cleave glucosylated hmN as described in Example 5.

Screening for Site-Specific Enzyme Reagents

Various substrates for screening enzymes of interest are described here. The first type of substrate described is naturally modified genomic DNA such as found in phage T4. Since natural modifications are commonly intended to prevent the genome of a parasite from cleavage by host enzymes, every hydroxymethylated base in the genome is modified. This substrate was found to be effective in screens for certain enzymes together with substrates from mutant phage that contain unmodified hmC only. Those enzymes which recognize a DNA sequence containing a single C and ignore hmC but are blocked by mhmC can be identified by the presence of cleavage products with the unmodified substrate only.

Natural substrates may not be suited for those enzymes which recognize DNA sequences containing multiple Cs but can cleave the DNA only in the presence of a single hmC. In these circumstances, it is desirable to create a synthetic double-stranded oligonucleotide substrate containing a single hmN. Methods for making two types of synthetic substrate are described herein. The first method generates short labeled fragments for easy recognition on a gel (see FIG. 2). The second method generates fragments of a length of greater than 50 nucleotides containing a hmN which is suited for amplification (see FIG. 7) and can serve both as a substrate for screening and as a control for locus analysis.

Generally, site-specific enzymes of interest for purposes described above may be identified by examining the NEB catalog or other commercial sources or by surveying REBASE® (NEB) (http://www.rebase.neb.com) to find endonucleases where the recognition sequences contain a specific nucleotide. Site-specific endonucleases are selected that cleave despite the occurrence of an mN or hmN in at least one given site within the recognition sequence, regardless of whether recognition or cleavage is blocked by methylation or hydroxymethylation at a different position in the recognition sequence. While most restriction endonucleases in REBASE have been screened for mC sensitivity, less is known about hmC sensitivity. Thus, candidate enzymes can further be tested for insensitivity to hmC using DNA derived from a mutant T4 bacteriophage, namely T4gt, in which all C residues have been replaced by hmC. The ability to cleave this DNA indicates further insensitivity to hmC. Selected enzymes that test positive for cleavage of T4gt DNA may be further tested for sensitivity to ghmC using T4 wt DNA, as shown in Examples 1-3, FIGS. 1A, 2A-2B, 3, 5, 6A-6F and 10 and Tables 1-3, to reveal the effect of glucosylation on enzyme recognition and cleavage. Similarly, candidate enzymes can be tested for insensitivity to hmU at the cleavage site using DNA derived from Bacillus phage SPO1 or its relatives in which T residues have been replaced by hmU (see Huang et al. *Nucleic Acids Res.* 10: 1579-1591 (1982)).

A screening assay that utilizes T4 phage DNA which is completely substituted either with ghmC (T4 wt) or hmC (T4gt) may not identify all suitable enzyme candidates. For example, enzymes with multiple C residues in the recognition site such as MspI (CCGG) may not cleave a DNA in which all C residues are methylated or hydroxymethylated. In fact, MspI cleaves DNA at a CCGG site only when the internal C is either unmethylated, methylated or hydroxymethylated and the external C is not methylated or hydroxymethylated.

Figure 2A:
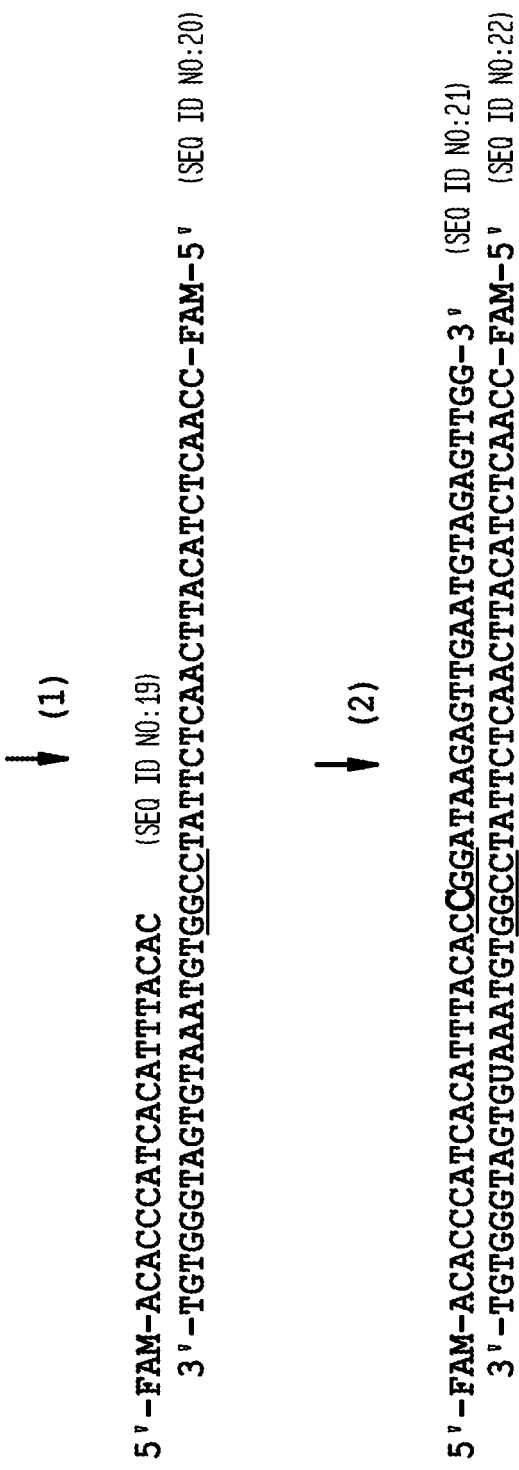
FIGS. 2A and 2B show the design and synthesis of oligonucleotides to test the sensitivity of MspI to hydroxymethylation of the central C in CCGG.
Figure 2B:
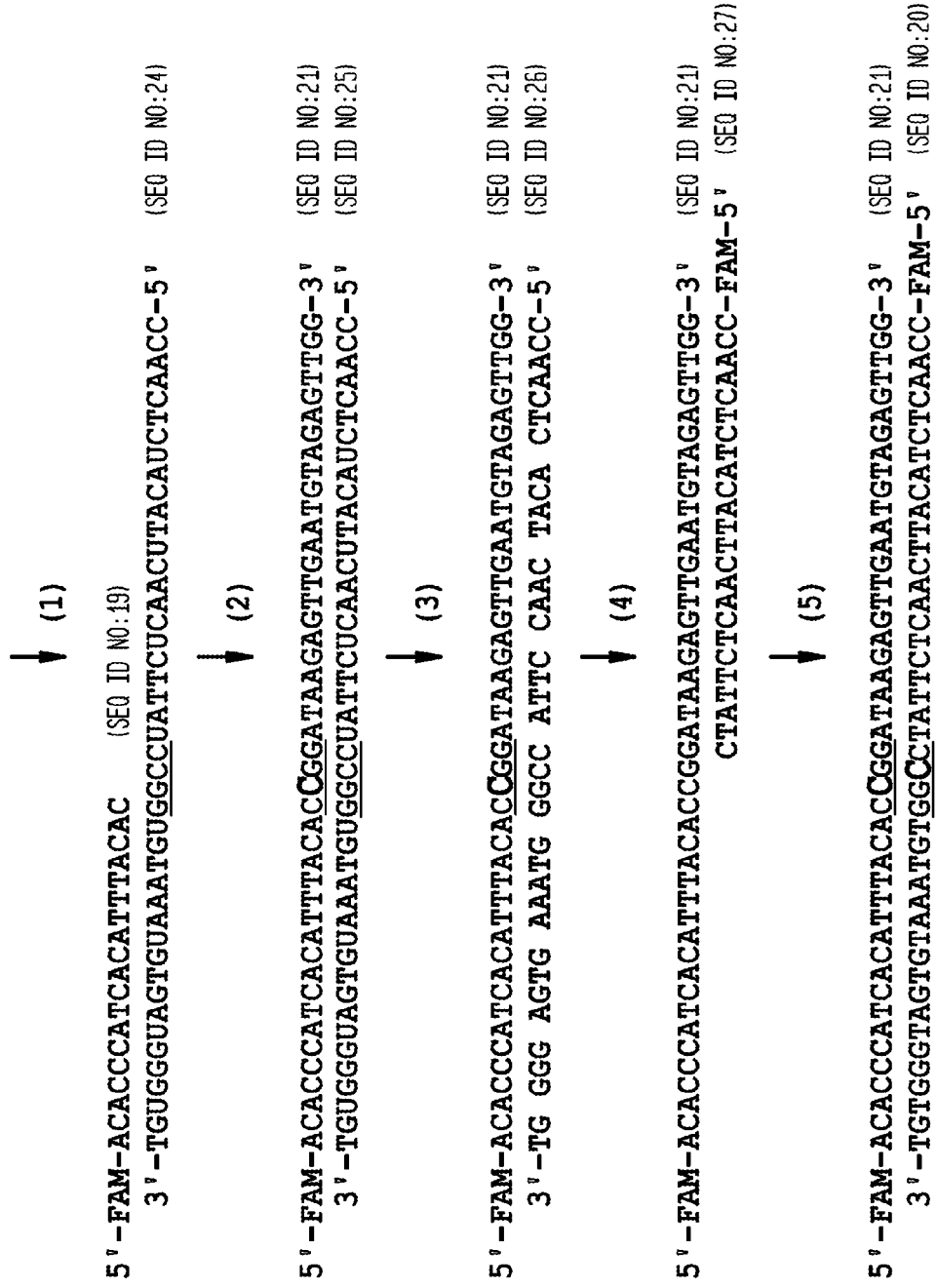

In the circumstances described above, it may be preferable to utilize a synthetic oligonucleotide having a known DNA sequence containing a hmN at a desired position (see for example, FIGS. 2A, 2B and 9).

The use of synthetic oligonucleotides in screening assays permits the identification of novel cleavage enzymes that may be suited for determining the location and number of mhmN in a genome.

Figure 4:
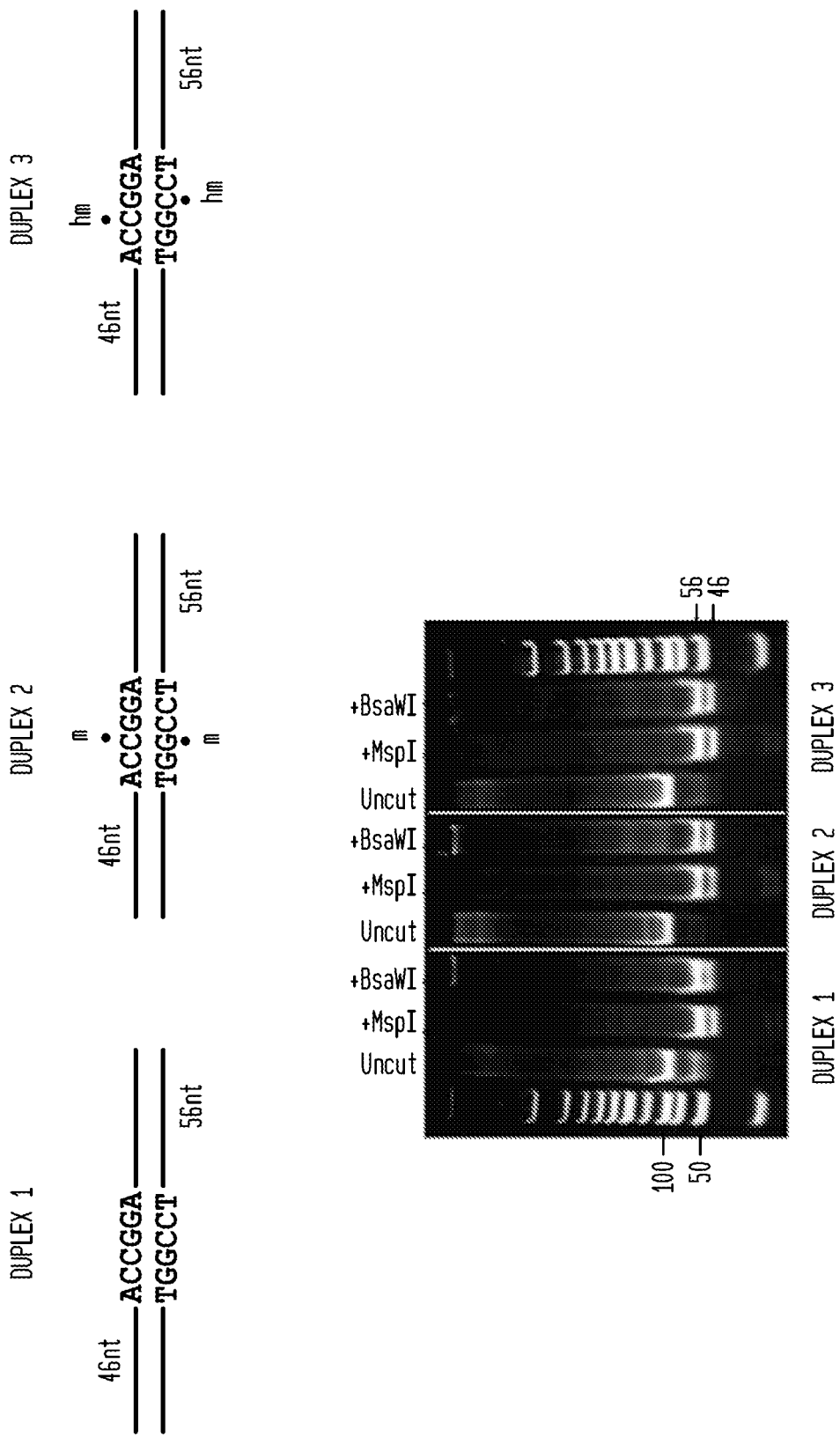
FIG. 4 shows the gel-based analysis of MspI and BsaWI cleavage demonstrating both to be insensitive to mC and hmC at the central position of their respective recognition sites, as evidenced by complete cleavage of the duplexes containing mC or hmC.
Figure 5:
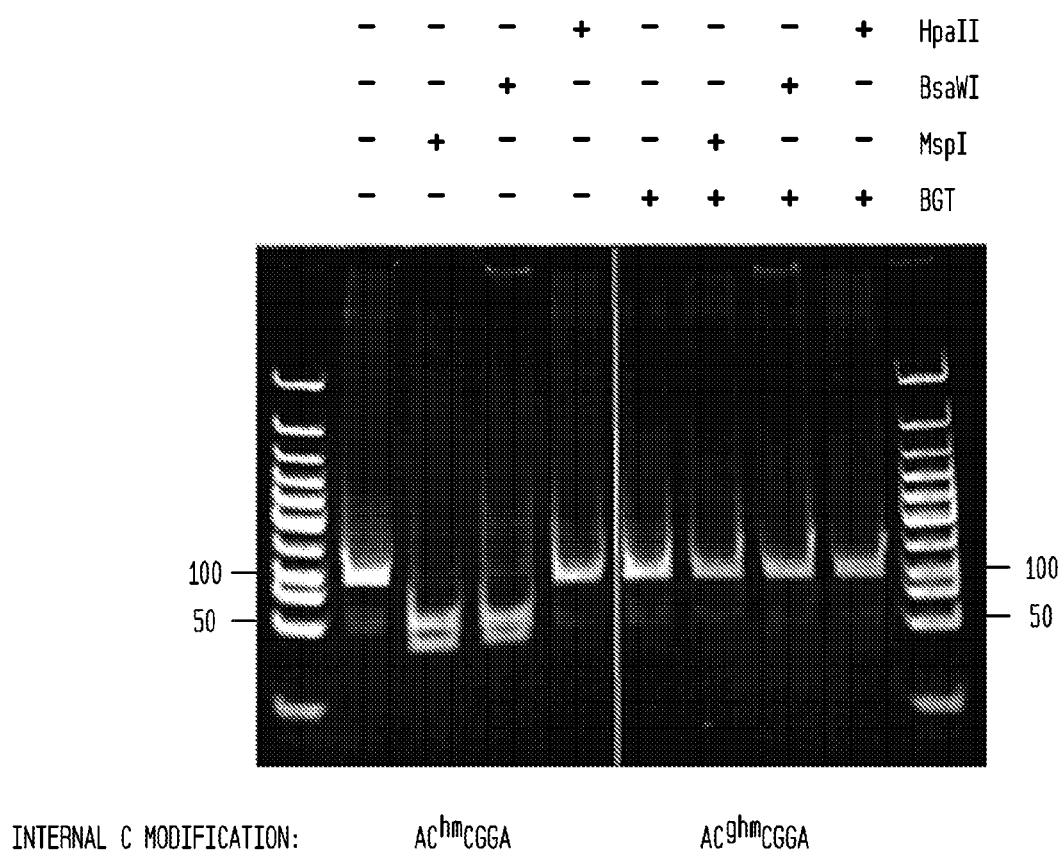
FIG. 5 shows that MspI and BsaWI do not cleave substrates containing ghmC in the central base pair of the recognition sequence. Substrates prepared as in FIGS. 2A and 2B with hmC were modified with BGT to create ghmC in the central base of the recognition sequence as described in Example 3. The site and identity of the internal C modification are defined below the lanes and correspond to $AC^{hm}CGGA$ and $AC^{ghm}CGGA$. A "+" above each lane indicates that the DNA has been treated with HpaII, BsaWI, MspI or BGT.
Figure 6:
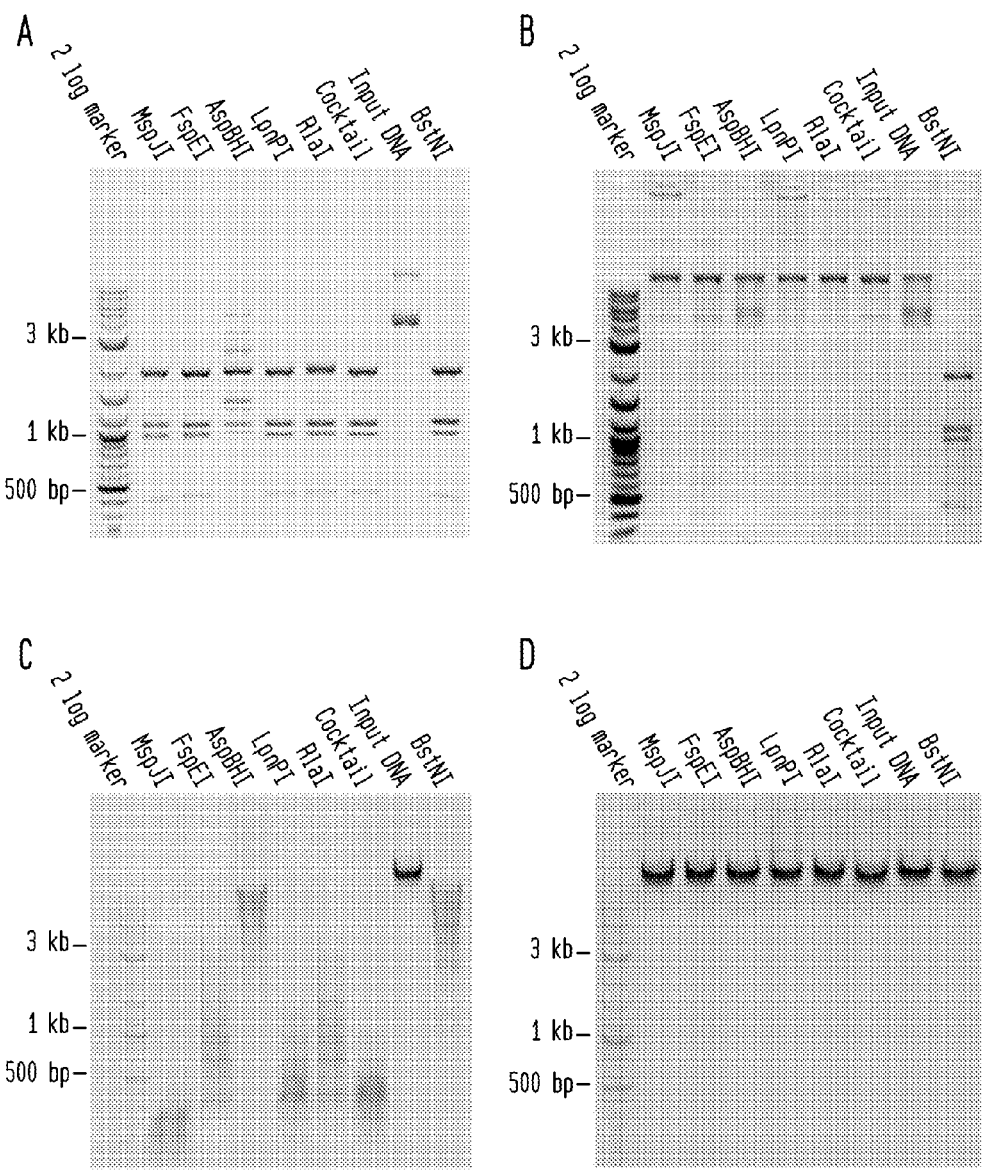
FIGS. 6A-6F show varying sensitivity in the activity of MspJI and homologs towards cytosine modifications. DNA was incubated at 37° C. with 1 unit of each of the specified enzyme as indicated on each lane, where "cocktail" refers to a mixture of all of the enzymes (0.2 unit each). Undigested DNA or DNA cleaved by BstNI (CC↓WGG) are controls.

Multiple enzymes in the individual classes specified above (for example see Tables 1-3) may be used to detect and quantify hmC. Alternatively, enzymes from different classes may be used together to obtain the desired result. For example, MspI and HpaII when used in parallel reactions, provide data on the occurrence of both mC and hmC in the dinucleotide CG embedded in the sequence CCGG. Various other nucleotide combinations can be found in a variety of alternative restriction endonuclease recognition sites that can be probed using cognate restriction endonucleases with appropriate selectivity towards hmC or other hmN, as described above. Use of such restriction endonucleases expands the repertoire of sites that could be examined in the genome (FIGS. 4, 5 and 6E and F).

Genome Analysis for Hydroxymethylation

The availability of selective tools for hmN permits detection and mapping of hmN to yield information about the status of gene expression of individual loci in a particular cell.

Detection and Mapping

Individual hmN residues may be identified and mapped on a reference genome that may already have mN locations identified or may be limited to a nucleotide sequence. A single hmN or cluster of hmN residues containing multiple hmN may be identified at a particular locus, and subsequent analysis allows mapping of that locus on a reference genome. A series of genome maps of hmN sites sampled at appropriate times can reveal how a pattern of hydroxymethylation changes over time and in changing environments, as well as among tissues differing in type, function, and disease state. The modification of hmN sites and the use of enzymes that differentially cleave or are inhibited by mhmN compared with hmN provide methods of creating a hydroxymethylome, enabling the monitoring of changes in hydroxymethylation at specific loci, thus facilitating the understanding of the significance of hydroxymethylation versus methylation in the genome. "Genomic DNA" as used here and in the claims refers to a DNA that is isolated from an organism or virus and is naturally occurring.

Using the reagents and the general approach described herein, identification and mapping of hmC in a DNA of interest can be accomplished by various methods that include the following:

(a) Site-specific reagents may be used for identifying hmN residues within isolated DNA fragments. For example, site-specific endonucleases may cleave at defined distances from the mN or hmN. This facilitates localization of hmN modification as the sequence context is identified in the course of sequence determination.

The MspJI family has been described in WO 2010/075375 and representative members have been characterized for example, MspJI, Sgrit 16873, Franean 1 (FspEI), Ipg1234 (LpnPI), AspBHI and RlaI. These endonucleases recognize C, mC or hmC and cleave at a distance (N12/N16). Each member of the class displays some preference for specific flanking nucleotides around the modified cytosine. All of them are able to cleave genomic DNA on both sides of a subset of symmetrically methylated sites to produce a set of homogeneously-sized fragments containing a centrally located mN or hmN. Interestingly, RlaI, an enzyme acting on mCWG but not on $^m$CpG sites, generates different digestion patterns between the plant and mammalian genomic DNA (see FIGS. 6E and F).

The cleavage fragments from the endonuclease digestion can then be ligated to external DNA sequences required for selective amplification and/or subsequent sequence analysis. Following ligation, samples are treated with an enzyme that selectively modifies hmN, but not mN. Subsequently, the modified samples are once again incubated with the site-specific endonuclease. DNA fragments containing mN are liberated from the ligated flanking sequences, and thus not amplified or analyzed in subsequent steps. In contrast, DNA fragments containing mhmN are not cleaved, and thus retain the ability to be amplified and/or sequenced using the ligated flanking sequences. (An example of this approach is provided in FIG. 7.) The use of different enzymes within the MspJI family allows interrogation of different subsets of sites and thus expands coverage of the methylome and hydroxymethylome. Deep sequencing of digested DNA fragments generated from these enzymes provides a means to map the majority of the modified sites in the genome.

Figure 8:
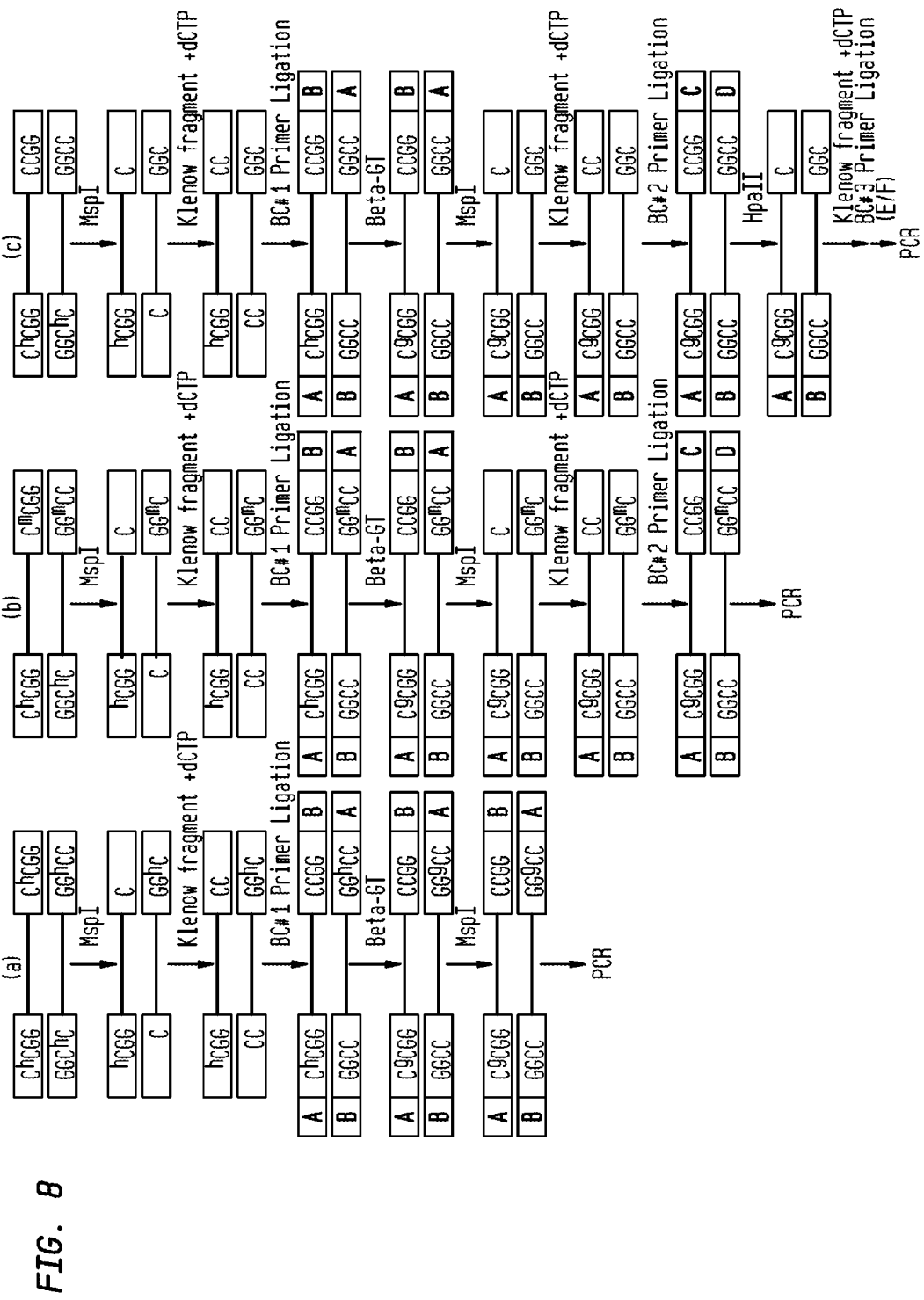
FIG. 8 shows a schematic of how to selectively detect CCGG, C$^m$CGG, and C$^{hm}$CGG sites in a DNA. The duplex sequence CCGG is illustrated with modification in both strands. Abbreviations are as follows: mC=$^m$C, hmC=$^{hm}$C, ghmC=$^g$C.

(b) DNA is fragmented by cleavage with a restriction endonuclease that is insensitive to mN or hmN within its recognition site, but whose cleavage is blocked when that site is modified. Fragmentation of genomic DNA by this enzyme is followed by ligation to flanking sequences designed to retain the sequence specificity and modification sensitivity of the restriction endonuclease. Samples are then treated with a second enzyme that selectively modifies hmN, but not mN. Subsequently, the modified samples are once again incubated with the restriction endonuclease. DNA fragments containing mN are liberated from the ligated flanking sequences, and thus not amplified or analyzed in subsequent steps. DNA fragments containing mhmN are not cleaved, and thus retain the ability to be amplified and/or sequenced using the ligated flanking sequences. (An example of this approach is shown in FIG. 8.)

Quantification of hmC at a Predetermined Locus in Cell Samples

A specific target region (locus) in the genome may be analyzed to determine the existence and/or extent of hmN modification. This may involve a quantitative analysis to allow assessment of the status of hydroxymethylation or the measurement of time-dependent changes in hydroxymethylation at selected loci in a population of non-identical genomes, for example, from a developing tissue or a diseased tissue from a mammal or a plant or from the genomes of bacteria or viruses.

Quantification can be achieved by analyzing specific sequences in fragments of the target sequence which may be generated by cleavage or primer-dependent amplification (such as qPCR) under conditions where (1) mC and hmC sites are retained, and (2) where only hmC sites are retained. This is illustrated in FIGS. 12-18.

In one embodiment, genomic DNA is subjected to two or more restriction endonucleases where at least one restriction endonuclease is insensitive to mN or hmN at a given site, but DNA cleavage activity is blocked when that site is ghmN. The DNA is sequentially or in parallel reacted with a second restriction endonuclease that recognizes the same site as the first endonuclease, but whose cleavage is blocked by the presence of mN.

For example, genomic DNA may be divided into two samples. Only one sample is treated with an enzyme that selectively modifies hmN. Treated and untreated samples are each separated into two pools, and then subjected to separate cleavage by the first and second restriction endonucleases. Cleavage within these four fractions of treated samples are then separately, but in parallel, analyzed using any method that determines the extent of site-specific cleavage in the target DNA.

In an embodiment, differentiating cleaved from uncleaved molecules may be carried out by a variety of methods known in the art. For example, cleavage patterns can be analyzed by Southern Blots in which fragments are generated, separated by gel electrophoresis, transferred to a membrane, and probed with labeled nucleic acids homologous to sequences at and around the locus of interest. Secondary restriction endonuclease cleavage may be used to further bracket the locus of interest. Nucleic acid arrays can also be employed in which arrays contain segments spanning the cleavage site.

Hybridization of cleaved loci may be less stable as fewer contiguous nucleotides will be available for hybridization. Molecular probes, employing hairpin structures whose fluorescent output is enhanced on DNA hybridization, but decreased in the absence of probes, can also be used to measure the cleavage state of the locus of interest. Alternative methods for determining the cleavage state of a specific site are known in the art, and could also be utilized.

Because the site-specific endonucleases used herein preferably cleave methylated and hydroxymethylated sites but not sites containing mhmN, the quantity of uncleaved modified DNA following first enzyme cleavage reflects the level of hydroxymethylation at the target sequence. Cleavage in parallel by a second site-specific endonuclease would occur only in case of an N, thus the quantity of uncleaved DNA following second enzyme cleavage of untreated (or modified) DNA reflects the combined levels of methylation and hydroxymethylation at the target sequence. The fraction of genomic DNA with mN or hmN at that locus can then be calculated (see Examples 12, 13, 14, 15 and 17).

Bioinformatic Analysis

Candidate loci may be identified by comparison of the derived sequences with a reference genome using bioinformatic methods known in the art, for example by BLAST comparison with UCSC hg18 (NCBI Build 36) which is a reference assembly for all human DNA sequence. The candidate loci from numerous samples may be determined using techniques such as deep sequencing (Shendure and Ji, *Nature Biotechnology* 26: 1135-1145 (2008)). It is envisaged that bioinformatic methods present in the art for determining suitable single nucleotide polymorphisms (SNPs) biomarkers may be applied to the analysis of hmC biomarkers. Techniques from other fields such as astronomy that analyze time-based signals to identify patterns may also provide data mining tools for recognizing patterns where structure is correlated with function.

Correlation of Location and Amount of hmN with Phenotype

Quantification of Ns, mNs, and hmNs in a target DNA sequence provides a useful data set for creating a statistical correlation between methylation and/or hydroxymethylation status and defined cell characteristics. "Hydroxymethylation status" as used here and in the claims refers to whether hydroxymethylation is present in the DNA or not. If hydroxymethylation is present, any of the amount and/or location of the mhmN can be determined. On a molecular level, such correlations can help reveal the function of the target DNA itself, including the impact of the modification on the function of neighboring sequences. Such analysis also can identify biomarkers predictive and diagnostic of normal and altered cellular states Based on the correlations, assays for hmN provide diagnostic and clinical tools for detecting and diagnosing aberrant cell types that will facilitate study and treatment of a variety of medically relevant states (see, for example, FIGS. 13 and 16 and Example 19).

When various stages of development are analyzed, differences are seen in the extent, location, and pattern of modification. The dynamics of changing between modified and unmodified states can thus serve as milestones to gauge the transition between cell types. In a similar sense, changes in modification state will also mark the transformation of normal, healthy cells into a disease state, such as cancer. As such, monitoring the changes in modification can serve as an early diagnostic prognosticator. In this context, the ability to monitor and measure site-specific changes in modification takes on increased importance, not only as a marker for cell type, but also as a marker and predictor for cell fate.

Other Nucleotide Modifications

Embodiments of the invention focus on hydroxymethylation in the context of the primary modification found in mammals, namely 5-mC in the dinucleotide CG. "Mammals" as used here and in the claims refers to its normal meaning and includes humans. It will be readily appreciated that this approach could also be used to analyze hydroxymethyl derivatives of mC found in alternate sequence contexts. For example, mC in plants is found in CG, CHG, and CHH, where H represents A, C, or T. Similarly, hydroxyderivatives of other modifications e.g. hmU can be analyzed for example by using glucosyltransferases from Trypanosomes (Gommers-Ampt et al. *Cell* 75: 1129-1136 (1993)) and oxidizing enzymes that convert thymidine to hmU (Cliffe et al. *Nucleic Acids Res.* 37(5): 1452-1462 (2009)).

The above-described methods would utilize the appropriate reagents for the alternate sequence contexts. Such reagents could be identified using the principles outlined above and in the examples.

Moreover, while mC is described in the examples, biological methylation has been observed at N4 of cytosine and the N6 of adenine. Such methylation is involved in bacterial restriction modification systems, and N6-methyladenine plays a role in regulating gene expression and DNA replication, as well as targeting mismatch repair to the newly synthesized DNA strand. The reagents described herein make possible analysis of the occurrence and distribution of these hydroxymethylated residues.

Use of Hydroxymethylation Detection and Quantification for Diagnosis of Disease and for Evaluating the Efficacy of Therapeutic Treatments Detection of hydroxymethylation as an indicator of deregulation of gene expression that gives rise to pathologies such as cancer may be achieved using the methods described herein. It is expected that hydroxymethylation status will provide useful prognostic information for the patient. The role of hypermethylation in cancer is described in WO 2010/037001. It is envisaged that a tissue sample will be analyzed for a hydroxymethylation status at a single locus or multiple loci to provide detection data. Detection data may be quantified and compared with data that is retrieved from a database over a network or at a computer station. The quantified data may be evaluated in view of retrieved data and a medical condition determined. This quantified data may be used to update the database stored at a central location or on the network where the database contains correlations of hydroxymethylation and disease status. The technology of data analysis and database creation of genomic data for determining a biological condition has been described for example in U.S. Pat. No. 6,692,916 for gene expression profiles using measurements of amounts of RNA transcripts. The methods described in U.S. Pat. No. 6,960,439 and U.S. Pat. No. 6,692,916 may be similarly applied to analysis of detection data of hydroxymethylation where hydroxymethylation at a locus in or outside of a gene determines whether transcription occurs. References describing the implications of detection of methylated nucleotides in the genome are also applied here to the detection of hydroxymethylated nucleotides in the genome (see for example, U.S. Pat. No. 7,662,563; US 2010-0151468, 2010-0172880, 2009-0317801).

All references cited herein, as well as U.S. provisional application Ser. Nos. 61/275,136 filed Aug. 25, 2009, 61/254, 346 filed Oct. 23, 2009, 61/296,630 filed Jan. 20, 2010, 61/296,630 filed Jan. 20, 2010, 61/354,826 filed Jun. 15, 2010, and 61/354,861 filed Jun. 15, 2010, are herein incorporated by reference.

EXAMPLES

Example 1

Screening for Site-Specific Endonucleases that Distinguish mhmN from mN

The genome of T4 wt phage contains completely substituted cytosine residues with hmC residues esterified with glucose in α or β linkages. T4gt phage DNA is not a substrate for the majority of restriction endonucleases (Huang, et al. *Nucleic Acids Research* 10: 1579-1591 (1982)). Mutant T4 phage in which cytosine residues are completely substituted with hmC are not esterified with glucose.

Site-specific endonucleases that are current commercial products of NEB were individually tested for their ability to cleave glucosylated T4 wt and non-glucosylated T4gt phage DNA. In each case, 0.5 μg of virion T4 DNA was digested for 1 and 18 hours under the supplier recommended reaction conditions with 1 μl of the respective restriction enzyme (NEB). Digestion products were then separated by agarose gel electrophoresis, using ethidium bromide staining and UV illumination to detect the products.

FIGS. 1A and 1B show representative results obtained from digestion with 14 restriction endonucleases that contain at least one C residue in their recognition sequence, including AflIII [ACRYGT], CviQI [G/TAC], NsiI [ATGCA/T], PciI [ACATGT], ScaI [AGT/ACT], EcoPI51 [CAGCAG], BspH1 [T/CATGA], CviAII [C/ATG], HpaI [GTTAAC], HinfI [G/ANTC], MboII [GAAGA(8/7)], MfeI [C/AATTG], RsaI [GT/AC] and XmnI [GAAN(4)TTC]. No change in the migration pattern of the fully modified T4 wt phage DNA was noted after incubation with any of these restriction endonucleases, and thus T4 wt DNA is refractory to cleavage by these enzymes. Eight restriction endonucleases, CviQI, NsiI, CviAII, HinfI, MboII, MfeI, RsaI and XmnI, produced smaller DNA fragments upon incubation with T4gt DNA, indicating at least partial cleavage insensitivity to hmC in their recognition sequence.

A listing of site-specific endonucleases that cleaved T4gt DNA, but did not cleave T4 wt DNA, is presented in Table 1. Each of these endonucleases can be used to probe for the occurrence of hmC in the sequence context of their recognition site.

TABLE 1

Enzymes that cleave T4gt DNA but not T4wt DNA are not sensitive to hmC but are sensitive to glucosylation

| Restriction Endonuclease | Recognition Site |
|---|---|
| BccI | CCATC(4/5) |
| BciVI | GTATCC(6/5) |
| BspHI | T/CATGA |
| BspQI | GCTCTTC(1/4) |
| BstEII | G/GTNACC |
| BstNI | CC/WGG |
| BstYI | R/GATCY |
| BstCI | GGCC |
| CviAII | C/ATG |
| CviQI | G/TAC |
| DpnI | GA/TC |
| EcoRI | G/AATTC |
| HinfI | G/ANTC |
| Hpy188I | TCN/GA |
| Hpy188III | TC/NNGA |
| MboII | GAAGA(8/7) |
| MfeI | C/AATTG |
| MlyI | GAGTC(5/5) |
| NsiI | ATGCA/T |
| RsaI | GT/AC |
| ScaI | AGT/ACT |
| SfcI | C/TRYAG |
| SmlI | C/TYRAG |
| Tsp45I | /GTSAC |
| XbaI | T/CTAGA |

Example 2

Preparation of Synthetic Oligonucleotide Substrates for Determining Cleavage where Only a Specific hmC and not a Plurality of hmCs is Present in a Recognition Site of a Site-Specific Endonuclease It was found that MspI failed to cleave T4gt substrate, which is hydroxymethylated and not glucosylated. It was theorized that fully hydroxymethylated phage DNA substrate may have an inhibitory effect on restriction endonuclease cleavage if additional hmCs are present within the respective recognition sequences that are located outside the CpG dinucleotide.

To overcome this problem, a FAM-labeled oligonucleotide substrate was developed that was validated using MspI to cleave hmC. The method for generating these substrates is shown in FIGS. 2A and 2B and is described below.

Duplex 1 (FIG. 2A) contained a single hmC residue within the duplex sequence 5' $C^{hm}$CGG 3'/3' GGCC 5'. Duplex 2 (FIG. 2B) contained two hmC residues positioned within the opposite strands of the duplex recognition sequence 5' $C^{hm}$CGG 3'/3' GG$^{hm}$CC 5'. To generate Duplex 1, a FAM-labeled oligonucleotide, 5'-FAM-ACACCCATCACATTTACAC-3' (SEQ ID NO:19), was annealed to a 45-nt template oligo 5' FAM-CCAACTCTACATTCAACTCTTATCCGGT-GTAAATGTGATGGGTGT-3' (SEQ ID NO:20), and filled in using a Klenow fragment and dATP, dTTP, dGTP and $d^{hm}$CTP.

To generate Duplex 2, a 45 nt template oligonucleotide was synthesized with 8 evenly distributed deoxyuracil residues: 5'-CCAACUCTACAUTCAACUCTTAUCCG-GUGTAAAUGTGAUGGGUGT-3' (SEQ ID NO:42). A FAM-labeled complementary oligonucleotide, 5'-FAM-ACACCCATCACATTTACAC-3'(SEQ ID NO:19), was annealed to a 45-nt template oligonucleotide and termini repaired using a Klenow fragment and dATP, dTTP, dGTP and $d^{hm}$CTP to generate an intermediate duplex with a single hmC residue within the sequence 5' $C^{hm}$CGG 3'/3' GGCC 5' (FIG. 2B, steps 1 and 2). The intermediate duplex was treated with USER™ (NEB) enzyme to excise uracil residues, thus removing the bottom strand (FIG. 2B, step 3). Next, a FAM-labeled complementary oligonucleotide, 5'-FAM-CCAACTCTACATTCAACTCTTATC-3' (SEQ ID NO:27), was annealed to the top strand and filled in using Klenow fragment and dATP, dTTP, dGTP and $d^{hm}$CTP to generate Duplex 2 (FIG. 2B, steps 4 and 5).

Figure 3:
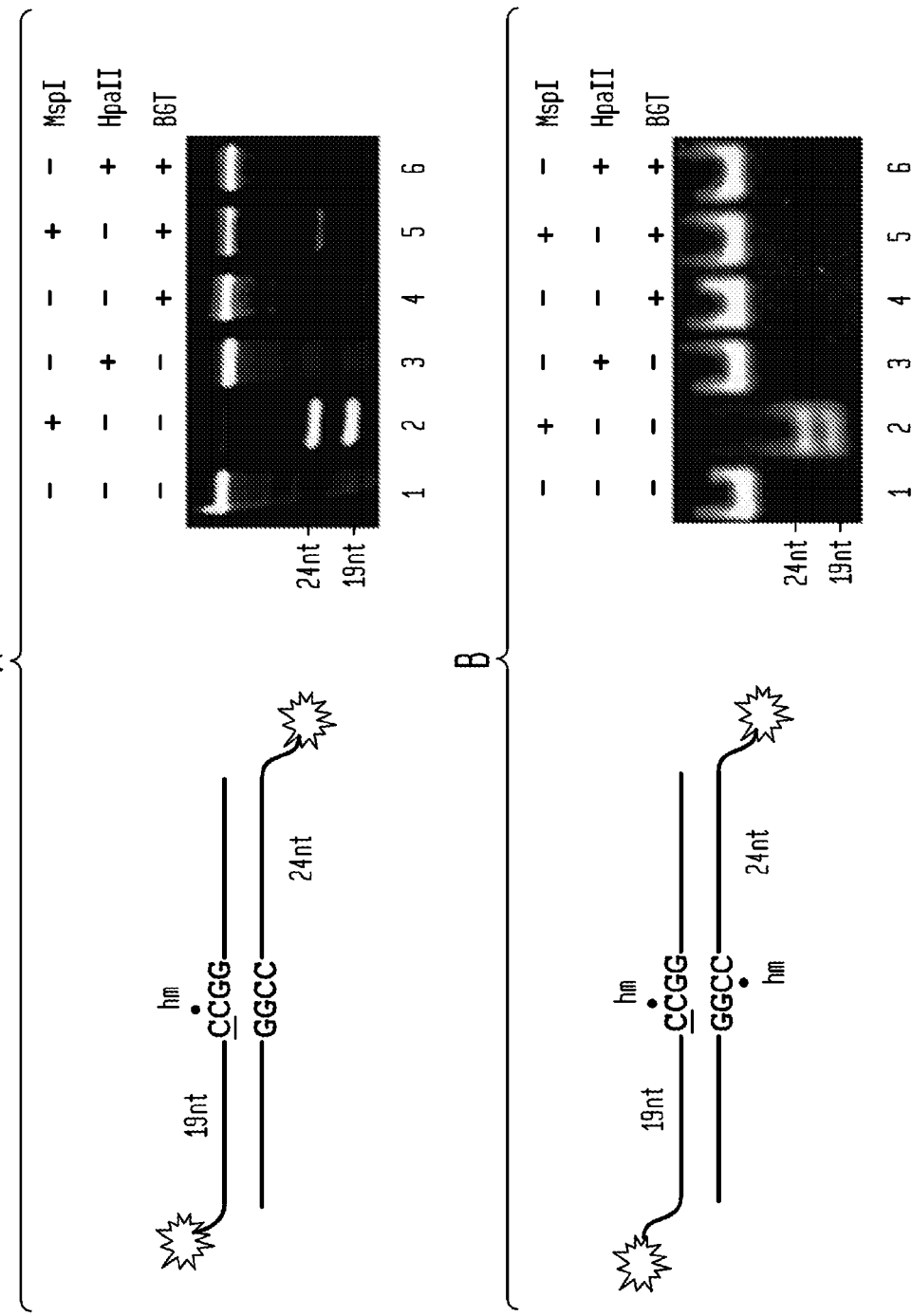
FIG. 3A shows the duplex I substrate which has a $C^{hm}CGG$ on one strand of the duplex only. A fluorescein (FAM) label is attached to both strands of the duplex at their termini. When this substrate is cleaved with MspI or HpaII or glucosylated with BGT in various combinations, the presence of a 24 nt and 19 nt labeled band is indicative of enzyme cleavage. Reaction products were separated by gel electrophoresis on a denaturing acrylamide gel for hemi-hydroxymethylated DNA. The results show that MspI cuts $C^{hm}CGG$, but not $C^{ghm}CGG$ DNA.
FIG. 3B shows the duplex 2 substrate which has a $C^{hm}CGG$ on both strands of the duplex. A FAM label is attached to both strands of the duplex at their termini. When this substrate is cleaved with MspI or HpaII or glucosylated with BGT in various combinations, the presence of a 24 nt and 19 nt labeled band is indicative of enzyme cleavage. Reaction products were separated by gel electrophoresis on a non-denaturing acrylamide gel for double hydroxymethylated DNA. The results are consistent with FIG. 3A, namely, that MspI cuts $C^{hm}CGG$, but not $C^{ghm}CGG$ DNA.

5 nmol/50 µl of Duplexes 1 and 2 were glucosylated using BGT (300 activity units, NEB) for 1 hour at 37° C. 10 µmol/10 µl non-glucosylated (FIG. 3 top and bottom, lanes 1-3) and glucosylated (FIG. 3 top and bottom, lanes 4-6) duplexes were cleaved with MspI and HpaII restriction endonucleases and the cleavage products were separated by electrophoresis on 10-20% polyacrylamide gels. The results presented in FIG. 3, lanes 3 and 6 demonstrated that HpaII restriction endonuclease cleaved neither non-glucosylated (lanes 3 upper and lower), hemi-glucosylated (lane 6 lower panel), nor fully-glucosylated (lane 6 upper panel) duplex sequences, indicating that the hmC residue present at the central base pair of the CCGG sequence had an inhibitory effect on HpaII (lanes 3 and 6). In contrast, MspI restriction endonuclease was capable of cleaving both hmC-containing substrates (FIG. 3, upper and lower panel, lanes 2), but was inhibited by glucosylation of either one or both of the hmC residues (FIG. 3, lane 5). A small amount (~5-10%) of 24-nt cleavage product was observed when hemihydroxymethylated duplex 1 was treated with MspI (FIG. 3, upper panel, lane 5) indicating that MspI is capable of slowly nicking a double-stranded recognition site, $C^{hm}$CGG/CCGG, in the unmodified strand. Other synthetic substrates were designed to detect hmC cleavage by other representative enzymes identified in Table 2 to cleave at an hmC. The results for BsaWI using this substrate is given in Example 3.

Example 3

The Effect of hmC and ghmC at the Central Base Pair of the BsaWI Recognition Site on BsaWI Cleavage The methods described in Example 2 may be used to screen for enzymes that did not cleave T4gt using the substrates described in Example 2 and FIG. 9. Examples of restriction enzymes that are insensitive to CpG methylation within their recognition sequences are provided in Table 2. This table is not intended to be exhaustive.

For example, the restriction endonuclease BsaWI (recognition site WCCGGW, where W=A or T) did not cleave T4gt DNA. Therefore, we tested BsaWI for the ability to cleave DNA when only the inner C is replaced by hmC in both strands of a double-stranded sequence 5'-A$C^{hm}$CGGT-3'/3'-A$C^{hm}$CGGT-5'. Using a similar approach to that used in Example 2, and the methodology outlined in FIG. 9, three 102 bp-long duplexes were prepared in which the central cytosine residue in the sequence ACCGGA was either C (duplex 1), mC (duplex 2), or hmC (duplex 3) (see FIG. 9). These three duplexes were reacted with MspI or BsaWI under standard reaction conditions: 0.1 µg of each duplex was digested in 20 µl of NEBuffer 4 (NEB) with either 100 units of MspI or 10 units of BsaWI for 1 hour at either 37° C. (MspI) or 60° C. (BsaWI). The cleavage products were separated by electrophoresis on 10-20% non-denaturing acrylamide gels and visualized by UV after staining with ethidium bromide. A gel is shown in FIG. 4 demonstrating that both MspI and BsaWI are insensitive to mC and hmC at the central position of their respective recognition sites, as evidenced by complete cleavage of the modified duplexes when compared to the control unmodified duplex.

Whether glucosylation of the hmC at this position would block the cleavage by BsaWI was tested. Duplex 3 was prepared with ghmC in the central C base of the recognition sequence using β-glucosyltransferase as described above. Substrates containing hmC or ghmC were incubated with either MspI or BsaWI (cleavage conditions were the same as described above), as shown in FIG. 5. Duplexes containing ghmC were resistant to cleavage by both enzymes, while those containing hmC were readily cleaved. The results indicate that BsaWI restriction endonuclease exhibits an inner cytosine modification sensitivity pattern similar to that of MspI and therefore may be used for detection of hmC in double-stranded DNA. In addition to BsaWI, the enzymes listed below are expected to cleave at sites containing hmC.

TABLE 2

Restriction endonucleases which cleave recognition sites containing $^m$CG, but do not cleave T4gt DNA

| Enzyme | Recognition site |
| --- | --- |
| BsaWI | W/CCGGW |
| BsoBI | C/YCGRG |
| BspEI | T/CCGGA |
| BssI | GGNNCC |
| BtgZI | GCGATG(10/14) |
| EciI | GGCGGA(11/9) |
| MspI | C/CGG |
| NmeAII | GATC |
| PspXI | VC/TCGAGB |
| TliI | C/TCGAG |
| XhoI | C/TCGAG |
| XmaI | C/CCGGG |

Example 4

Determination of the Variations in Recognition Specificities for the MspJI Class of Endonucleases The MspJI family of site-specific endonucleases are described in WO 2010/075375. The use of enzymes from this family are used here to expand the detection of hmN in the genome.

A qualitative comparison of genomes with varied methylation levels demonstrated that the MspJI family of enzymes could be differentiated by their cleavage products (see FIGS. 6A-6F). For example, CpG methylation in mammalian genomes can be differentiated from CHG methylation in plants using cleavage patterns derived from use of RsaI (FIG. 6F).

Biochemical characterization of MspJI, FspEI, LpnPI, AspBHI and RlaI was carried out using synthetic oligonucleotides. These enzymes recognize C5 modification (methylation or hydroxymethylation) of cytosine and cleave ($N_{12}/N_{16}$) away from the modified cytosine, similar to MspJI. However, the specificity of the MspJI family appears to vary with respect to preferences in flanking nucleotides around the modified cytosine (Table 3). All endonucleases are able to cleave genomic DNA on both sides of symmetrically methylated sites to produce small fragments containing centrally located hmNs or mNs.

The sequence for the homologs of MspJI including FspEI, LpnPI, AspBHI and RlaI, were obtained from GenBank and then codon optimized and synthesized by using a standard overlapping oligonucleotide assembly method. Recombinant enzyme with N-terminal His-tag were then expressed in dcm⁻ E. coli T7 Express (NEB) and purified to apparent homogeneity.

TABLE 3

Recognition sequence specificity of MspJI homologs as determined by use of synthetic oligonucleotide substrates

| Enz. name | Species | Recognition site w/o activator | Recognition site w/ activator |
| --- | --- | --- | --- |
| MspJI | Mycobacterium sp. JLS | $^m$CNNR | $^m$CNNR |
| FspEI | Frankia sp. EAN1pec | C$^m$C | C$^m$C or $^m$CDS |
| LpnPI | Legionella pneumophila Philadelphia 1 | C$^m$CDG | S$^m$CD or $^m$CDS or C$^m$C |
| RlaI | Ruminococcus lactaris ATCC 29176 | V$^m$CWG | V$^m$CWS |

Example 5

Type IV Restriction Endonucleases that Distinguish Modified hmN from mN

Specific cleavage by a site-specific endonuclease in response to the presence of ghmC permits the assignment of specific hmC modifications to specific genomic loci. Conversion of hmC residues in a DNA sample to ghmC by a glucosyltransferase permits the generation of fragments which can be sequenced (for example, using massively parallel sequencing) to determine the original site of the hmC residue (e.g., Zeschnigk, et al., Hum Mol Genet 18(8): 1439-48 (2009); Volkening, et al., J Virol Methods 157(1): 55-61 (2009)).

An example of a site-specific endonuclease specific for ghmC-containing DNA is the Type IV restriction endonuclease GmrSD (Bair, et al. Journal of Molecular Biology 366(3): 768-78 (2007)). This enzyme is capable of cleaving DNA bearing ghmC in both alpha and beta configurations. Mapping of these cleavage sites against a reference genome provides a tool for identification of ghmC residues responsible for the cleavage. Accordingly, sites of hmC modification in a genome can be inferred by analyzing a genome in which hmC has been converted to ghmC, subsequently cut by GmrSD, and the identity of fragment ends revealed by DNA sequencing.

An appropriate protocol to determine what sequence lies adjacent to the ghmC residues involves some or all the following steps:

1) purification of GmrSD;
2) isolation of DNA or nuclei from cells to be tested;
3) treatment of the isolated DNA or nuclei with a glucosyltransferase and appropriate substrate, for example AGT or BGT from bacteriophage T4 in the presence of UDP-Glc;
4) cleavage in vitro or in situ by GmrSD;
5) DNA end repair to render DNA termini suitable for ligation;
6) ligation of an oligonucleotide bearing a primer-binding site to the end repaired termini and optionally having a purification tag, such as biotin) (for in-situ ligation, see Ribeiro, et al. Mol Biol Cell 17(10): 4584-91 (2006); and Frustaci, et al. Mod Pathol 19(6): 755-65 (2006));
7) purification of DNA attached to the oligonucleotide;
8) linear amplification with a primer, which anneals to the oligonucleotide and may carry a purification tag;

9) treatment to fragment the DNA, such as sonication or digestion with non-specific DNAse;
10) size-fractionation;
11) DNA end repair to render DNA termini suitable for ligation;
12) ligation to the collected DNA fragments of a second oligonucleotide bearing a second primer-binding site;
13) purification by means of the tag used on the first oligonucleotide or the first primer; and
14) DNA sequence determination by a suitable method.

The linear amplification in step 8 enriches for short sequences adjacent to the GmrSD cleavage site, increasing the yield of sequences obtained from the anonymous region of interest. Purification of DNA at steps 7 and 13 increases the yield of the sequence of interest.

Example 6

Chemical Method for Detection of Glucosylated Hydroxymethylated DNA

The glucose portion of the ghmC residue is susceptible to oxidization by sodium periodate, resulting in ring opening and introduction of aldehyde functionalities at C2 and C3 (FIG. 20). Following dialysis to remove excess periodate, the ring-opened species can be reacted with biotin-LC-hydrazide (Thermo/Pierce cat. #21340, Rockford, Ill.), resulting in addition of biotin to both C2 and C3 via a stable hydrazone linkage (FIG. 20). The resulting biotinylated DNA can be detected or captured using labeled streptavidin or anti-biotin antibodies. As an alternative to biotin hydrazide, the corresponding hydrazide of any other reporter group (e.g., fluorescent dyes) can also be prepared, resulting in specific labeling of ghmC lesions with that reporter group. (Bayer et al. *Anal. Biochem.* 170, 271-281 (1998); Thermo/Pierce technical bulletin, EZ-Link Biotin Hydrazides, #0124.5).

Example 7

Use of BGT and the MspJI Family of Enzymes for Discovery of Loci Containing hmC

Figure 7:
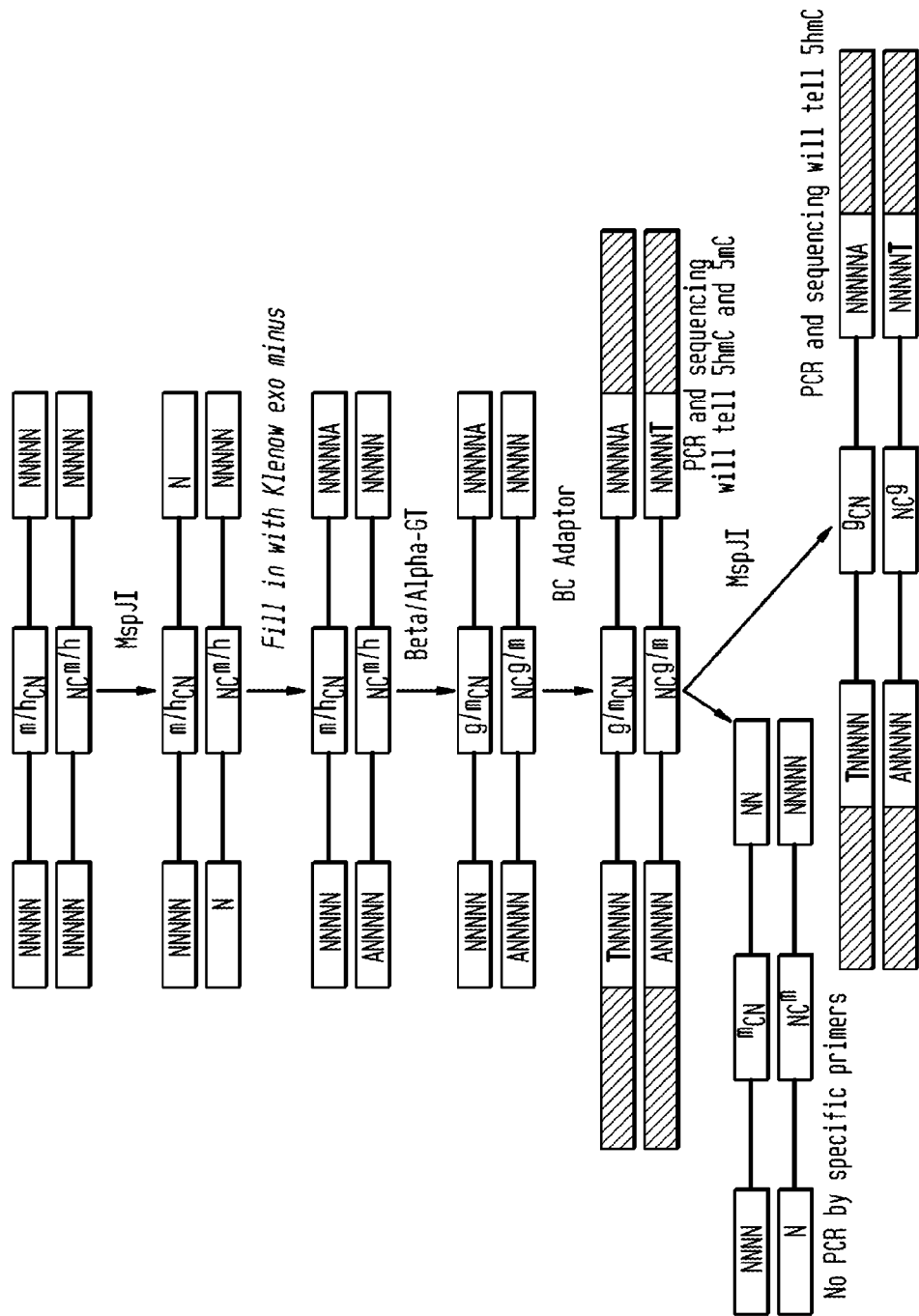
FIG. 7 shows a schematic for isolation of DNA fragments containing ghmC in duplex DNA using MspJI and BGT. Cleavage of genomic DNA at CpG sites creates ~32 bp duplex DNA fragments with a centrally located mC or hmC (denoted as $^{m/hm}C$) and with 4 nucleotide 5' overhangs at the termini. This collection of fragments is treated with Klenow exo$^-$ DNA polymerase (Klenow exo$^-$), effectively filling in the overhang and adding an additional untemplated 3'A residue. The sample is treated with either BGT or AGT and UDP-Glucose (UDP-Glu or UDP-Glc), converting hmC residues to ghmC ($^gC$). Adapters containing a single 3'T residue are ligated to the pool of DNA fragments using a Barcoded (BC) adaptor, and the ligated population is digested with MspJI. Amplification of this treated library, required for sequencing, will only recover those fragments with adapters remaining at both termini, namely, those containing hmC that have been converted to ghmC.

Although MspJI cuts at mC and hmC residues, ghmC residues do not support cleavage. This fact is used here in a method that illustrates how to detect hmC sites within a genome. As illustrated in FIG. 7, for this analysis, genomic DNA samples are cut with MspJI and, after any required modification of the termini, ligated to duplex DNA primers. This pool is then treated with β-glucosyltransferase, and subsequently again digested with MspJI. Ligation products with mC are again cut by MspJI, thus excising the duplex primers. Ligation products with ghmC (originally hmC) are not be cut, and are used as substrates for subsequent amplification and/or sequence analysis.

A reaction mixture containing 2-10 μg of genomic DNA (containing mC and/or hmC) is digested at 37° C. with 4-50 units of MspJI (NEB), 0.5 μM activator with 1×NEB4 reaction buffer (NEB) in a volume of 25-500 μl for 12-16 hrs (overnight) or until complete digestion is obtained. Digested DNA is phenol:chloroform-extracted, ethanol-precipitated, and suspended in TE buffer. This DNA is mixed with 6× gel loading dye (NEB) and separated on a 20% polyacrylamide TBE gel (Life Technologies, Carlsbad, Calif.) in parallel with a suitable DNA molecular weight marker (NEB). The DNA marker lane is excised from the gel and stained with SYBER® gold (Life Technologies). The stained ladder is used as a marker/ruler to guide excision of DNA from genomic DNA-digested samples in the size range of 26-40 bp. DNA is isolated and purified from the acrylamide gel segments using a crush and soak method (Lewis *Biotechniques* 21: 820-822 (1996)) followed by phenol:chloroform extraction and ethanol-precipitation in the presence of glycogen (Roche, Basel, Switzerland). The precipitated DNA is suspended in 0.1×TE buffer. The termini of the size-selected MspJI-digested DNA fragments are repaired, with an accompanying addition of an untemplated 3' terminal A residue, in a reaction containing 20 units Klenow fragment exo⁻ (NEB) in a 50 μl of reaction volume containing 0.4 mM dATP, 0.04 mM dCTP, 0.04 mM dGTP and 0.04 mM dTTP in 1×NEB2 buffer (NEB) for 15 min at 25° C. (room temperature), followed by 15 min at 37° C. The reaction products are purified using a nucleotide removal kit (Qiagen, Valencia, Calif.). Ligation to a pre-annealed Illumina (San Diego, Calif.) adaptor is performed using an Illumina DNA preparation kit. After adaptor ligation, the final adaptor-ligated DNA samples are incubated with 0.5 μg of either BGT or AGT (NEB), 1×NEB4 buffer (NEB), supplemented with 0.2 mM UDP-Glc, in a volume of 25-50 μl. The reaction products are heat-inactivated at 70° C. for 20 min. and treated with 2-4 units of MspJI to remove adapters from fragments containing mC instead of hmC. This removal also eliminates priming sites for subsequent PCR amplification, effectively removing fragments lacking hmC from the amplification pool. PCR is then performed to enrich/amplify the reaction products using a standard PCR protocol. These reaction product are sequenced using the Illumina platform or SOLiD™ (Life Technologies, Carlsbad, Calif.) for genome-wide hmC analysis (see FIG. 7).

Size-selected, isolated pools of such fragments can contain enough DNA information content to uniquely map the location of the mC or hmC residue within the fragment to a reference genome for a large majority of the fragment, at least in the case of the human genome.

Example 8

Detection of Asymmetric and Symmetric Methylation on a Polynucleotide Using MspJI A protocol in example 7 describes how hmC can be detected using MspJI. This methodology depends on the presence of hmC on both strands of the DNA duplex. A modification of the technique outlined in FIG. 7 allows for discovery of sites in which hmC modification occurs in a single strand of the DNA duplex. A difference is that dual methylation causes excision of a short duplex, whereas single methylation produces DNA fragmentation of variable size, dependent on the proximity of the adjacent modification site. Accordingly, MspJI cleaved-end-repaired DNA can be ligated to a sequencing/amplification adapter and then randomly sheared.

In a reaction mixture, 2-10 μg of genomic DNA (containing 5-mC and/or 5-hmC) is digested with a sufficient amount of MspJI to give complete digestion, typically 20-100 u (NEB) with reaction buffer in a volume of 25-500 μl for 12-16 hrs (overnight) at 37° C. Digested DNA is phenol:chloroform-extracted, ethanol precipitated, and suspended in TE buffer. The DNA termini are repaired and an untemplated 3'A residue added in a reaction containing 20 U Klenow fragment (NEB) in a 50 μl of reaction mixture containing 0.4 mM dATP, 0.04 mM dCTP, 0.04 mM dGTP and 0.04 mM dTTP in 1×NEB2 buffer (NEB) for 15 min at 25° C. (room temperature), followed by 15 min at 37° C. The resulting DNA is phenol:chloroform-extracted, ethanol precipitated, and suspended in 0.1×TE buffer. The suspended DNA product is ligated with double-stranded DNA adapter with T overhangs. The ligation reaction is performed using 20 U T4 DNA Ligase (NEB) in 1× ligase buffer in a total volume of 20 µl for 20 min at room temperature.

The reaction product is purified by Qiagen spin column (Qiagen, Valencia, Calif.) and sheared using enzymatic methods (e.g Fragmentase™, NEB), sonication, hydrodynamic, or acoustic methods (e.g., Covaris, USA, Woburn, Mass.) to a DNA sample size of 100-150 bp. The sheared DNA is end-repaired using the NEBNext® end repair module (NEB). The reaction products are purified by a spin column (Qiagen, USA) and a 3' terminal A residue added using the NEBNext dA-Tailing module. To this product is ligated a duplex adapter with T overhangs, where the adapter is specific for the high throughput sequencing platform (e.g., Illumina). The ligation reaction is performed using 20 U T4 DNA Ligase (NEB), 1× ligase buffer in a total volume of 20 µl for 20 min at room temperature. The samples are used for library amplification and sequencing, for example on an Illumina (San Diego, Calif.) platform for direct sequence determination. The identity of the 5-methylcytosine at both symmetric and asymmetrical positions can then be deduced by bioinformatics. For example, inserts are expected to contain a cytosine residue between positions 15-17 from the adapter sequence, as this cytosine corresponds to the mC residue required for MspJI cleavage. Fragment ends arising from shearing likely lack an appropriately positioned cytosine residue, particularly since CpG dinucleotide is underrepresented in the human genome. After discovery, the occurrence of mC and hmC can be verified by endpoint or Q-PCR methods detailed above.

Example 9

Use of MspJI or One of its Homologs to Interrogate a Particular Locus for the Presence of 5-mC or 5-hmC MspJI and its homologs recognize methylated CpG dinucleotides, and generate a cleavage fragment that is 32 bases in length having a 4-base overhang on either side. The 32-base long fragment will contain 8 bases of additional information in the overhangs. Thus, when it is desirable to interrogate a particular CpG dinucleotide, a pair of adapters can be designed such that following the initial enzyme cleavage event, the desired locus can be linked specifically to the adapters by ligation. These adapters can be designed quite flexibly, for instance by incorporating a tag such as biotin suitable for purification from the mixture and can also carry additional sequences so that the resulting 32-mers plus the adapters can be subjected to direct sequencing. The primers used for the sequencing are designed in such a way that they contain a) sequences complementary to the unique bases in the adapter plus b) the four bases that were used to determine the site of ligation and c) a few bases specific to the fragment on which the target resides (see FIG. 19). In this way, with the reference to the complete sequence of the human genome, a sequencing primer can then be extended uniquely to interrogate the methylation status of the target site. If the site is methylated (or hydroxymethylated), then an extension product will be produced that can be detected by sequencing, by hybridization or any of the standard ways of detecting oligonucleotides. To distinguish methylated from hydroxymethylated bases, the experiment is run in parallel with one sample being first treated with T4 BGT prior to cleavage with MspJI or one of its homologs and the second sample receiving no such treatment. Glucosylation prevents cleavage and so no 32-base long fragment will be present in the final mixture and no sequence extension product will be produced. It should be noted that because the two 4-base extensions on either side of the target CpG will be different, it is possible to design the interrogating primers so that both strands of the sequence can be interrogated independently. An alternative or additional way of differentiating mC from hmC at any individual target site utilizes PvuRts1I to digest the DNA prior to MspJI digestion. In this way, it is possible to selectively remove from the fragment mixture any fragments that contain 5-hmC. Alternatively, PvuRts1I can be used directly to selectively cleave genomic DNA at hmC.

Example 10

High-Throughput Approach to Discovering hmC-Containing Loci Using BGT and MspI

Next generation, high throughput sequencing may be used to identify loci containing one or more hmC. The approach described here allows detection of hmC in MspI sites regardless of whether the adjacent MspI sites are methylated or hydroxymethylated.

Alternate cycles of MspI cleavage, BGT treatment, and MspI cleavage are interspersed with PCR primer ligations to distinguish the various types of methylation at MspI sites (FIG. 8). The essential feature is the selective protection against MspI cleavage provided by ghmC within the site. Amplification and/or sequencing primers attached to such protected sites will be retained, and thus be present in the pool of sequenced products. Sites that are not protected will lose these amplification and/or sequencing primers and thus not be analyzed.

In a reaction mixture, 2-10 µg of genomic DNA (containing mC and/or hmC) is digested with 20-100 units of MspI (NEB) with reaction buffer in a volume of 25-500 µl for 12-16 hrs (overnight), or until completely digested, at 37° C. Digested DNA is phenol:chloroform-extracted, ethanol-precipitated, and suspended in TE buffer. Alternately, the digested DNA is spin column-purified. The purified DNA is reacted with 10 units of Klenow fragment, 1× reaction buffer and 0.4 mM dCTP. This step creates a one base 5'-C overhang. The dCTP-filled DNA is mixed with 6× gel loading dye (NEB, Ipswich, Mass.) and separated on a 4% NuSieve® agarose gel (Lonza, Basel, Switzerland), running in parallel a lane with a 50 bp DNA ladder (NEB, Ipswich, Mass.). The DNA ladder lane is excised from the gel and stained with SYBER® green (Invitrogen, now Life Technologies, Carlsbad, Calif.)/ethidium bromide. The stained ladder is used as a marker/ruler to guide excision of DNA sited between 40-300 bp from genomic DNA digested samples. DNA is purified from the agarose using a gel-purification spin column (Qiagen, Valencia, Calif.). This size-fractionated DNA is phenol:chloroform-extracted, ethanol-precipitated, and suspended in 0.1×TE buffer. The suspended, size-selected MspI-digested, dCTP-filled DNA is ligated to a double-stranded DNA adapter, BC#1 (A/B) (Table 4) that has termini with 5'-G overhangs, allowing ligation to recreate the MspI site. The ligase reaction utilizes 20 units T4 DNA Ligase (NEB) in 20 µl 1× ligase buffer, and is incubation for 20 min at room temperature.

Using the above method, the reaction product is purified by Qiagen spin column (Qiagen, Valencia, Calif.) and treated with 0.5 µg BGT or AGT (NEB), 1×NEB4 buffer (NEB), supplemented with 0.2 mM UDP-Glc, in a volume of 25-50 µl.

The reaction product is heat-inactivated at 70° C. for 20 min. and treated with 50 units MspI at 37° C. for 1 hr, heat-inactivated at 80° C. for 20 minutes, and fragments ranging in size from 60-400 bp are isolated using agarose gel electrophoresis as described above. A portion (approximately one-third) of the resulting DNA fragments are then subjected to sequence analysis, for example with an Illumina sequencing platform (Illumina, San Diego, Calif.). Only molecules in which the BC#1 (A/B) Primers (Table 4) are still attached to both strands will be amplified and sequenced by this process, and thus derived sequences will reflect adjacent MspI sites that are hmC-modified in the genomic DNA sample.

The remaining two-thirds of the sample are reacted with Klenow fragment and dCTP. The dCTP-filled DNA is ligated with double-stranded DNA BC#2 (C/D) (Table 4), which also recreates the MspI site due to the presence of a 5' G overhang and a flanking GC base pair. The ligase reaction is performed using 20 units T4 DNA Ligase (NEB) in 1×NEB ligase buffer in a total volume of 20 µl for 20 min at room temperature. Half of this sample is sequenced (Illumina) or PCR-amplified. Sequence adjacent to the BC#1 duplex will only be derived from genomic MspI sites originally containing hmC. Sequences derived from the opposite end of the insert fragment, i.e. adjacent to BC#2, are derived from MspI sites that are either unmodified, or which contain mC. In fact, this pool can be limited to those sites that contain mC by digestion prior to sequence analysis by HpaII, which will remove BC#2 from unmodified MspI sites. However, in the process fragments with adjacent hmC and unmodified MspI sites will also be lost.

Analysis can be further extended to MspI fragments containing one end modified by hmC, and the other being unmodified. Following the above BC#2 ligation, the remaining sample is heat-inactivated at 70° C. for 20 min and treated with 50 units HpaII at 37° C. for 1 hr, heat-inactivated at 65° C. for 20 minutes, and DNA fragments from 60-400 bp isolated as described above. Fragments are then treated with Klenow exo-in the presence of dCTP and ligated to a third adaptor pair, BC#3 (E/F) (Table 4). This sample is then sequenced at both ends (using for example, an Illumina sequencing platform) to determine 5-hmC at the CCGG site adjacent to unmethylated CCGG sites.

The combination or individual preparations are then amplified and the amplified products analyzed for the following:
(a) Amplification products with A/B-A/B termini ($C^{ghm}$-CGG-----$C^{ghm}$CGG)
(b) Amplification products with A/B-C/D termini ($C^{ghm}$-CGG------$C^{m}$CG); and
(c) Amplification products with A/B-E/F termini ($C^{ghm}$-CGG---CCGG).

TABLE 4

Primer and Adaptor Sequences

| Primer or adaptor | Sequence |
| --- | --- |
| MspJI adapter, top strand: | 5'ACACTCTTTCCCTACACGACGCTCTTCCGATCT (SEQ ID NO: 9) |
| MspJI adapter, bottom strand: | 5'-phosphate-GATCGGAAGAGCTCGTATGCCGTCTTCTGCTTG (SEQ ID NO: 10) |
| MspI compatible end adapter A of BC#1: | 5'ACACTCTTTCCCTACACGACGCTCTTCCGATCTGG (SEQ ID NO: 11) |
| MspI compatible end adapter B of BC#1: | 5'-phosphate-CAGATCGGAAGAGCTCGTATGCCGTCTTCTGCTTG (SEQ ID NO: 12) |
| MspI compatible end adapter C of BC#2: | 5'ACACTCTTTCCCTACACGACGCTCTTCCGATCTCACGG (SEQ ID NO: 13) |
| MspI compatible end adapter D of BC#2: | 5'-phosphate-CGTGAGATCGGAAGAGCTCGTATGCCGTCTTCTGCTTG (SEQ ID NO: 14) |
| MspI compatible end adapter E of BC#3: | 5'ACACTCTTTCCCTACACGACGCTCTTCCGATCTTATGG (SEQ ID NO: 15) |
| MspI compatible end adapter F of BC#4: | 5'-phosphate-CATAAGATCGGAAGAGCTCGTATGCCGTCTTCTGCTTG (SEQ ID NO: 16) |
| MspJI activator, top strand | 5'ATGGTCMAGGAGCCAG-Bt 3' (SEQ ID NO: 17) |
| MspJI activator, bottom strand | 5'TGGCTCMTGGACCATG-Bt 3' (SEQ ID NO: 18) |

The MspJI adaptors described in Table 4 have a single strand overhang of a length that is sufficient for hybridizing to the MspJI fragments as described in FIG. 7 and Example 9. The MspI adaptors are designed for use in the method described in this Example and FIG. 8.

A kit may be assembled for performing the locus identification described above. The kit may include a mixture of enzymes in a single reaction vessel or individual enzymes where the enzymes include MspI, a glucosyltransferase and optionally one or two or three different adapter pairs identified in FIG. 8 as A/B, C/D and E/F and Klenow fragment. The kit may further include reagents for amplification. Instructions for use may be provided to enable a user to perform the method described in this example.

Example 11

Discovering hmC-Containing Loci Using BGT and MspI

The differential sensitivity of MspI to hmC and ghmC in the CpG of the recognition sequence can be exploited to identify hmC-containing loci in a variety of genomic DNAs (see FIG. 8). MspI was used to fragment genomic DNA, which was then ligated to an unmodified, MspI-cut plasmid vector, recreating the MspI recognition site at each ligation junction. MspI sites derived from fragments with hmC retained the hmC status of the genomic MspI site, albeit in hemi-hmC form. Subjecting the ligated library to BGT generated ghmC, which conferred resistance to MspI cleavage. In contrast, library members in which no hmC was found in the MspI sites were linearized by treatment with MspI. As transformation into *E. coli* of linear molecules was much less efficient than for circular molecules, transformation of the MspI-cut library highly enriched the library for MspI fragments where both ends were hmC-modified in the genomic sample. Sequence determination of the termini of the library inserts allowed the assignment of the hmC residue to a specific locus on the reference genome.

To test this scheme, genomic DNA from mouse E14 embryonic stem cells (Wakayama et al. *Proc Natl Acad Sci USA* 96: 14984-9 (1999)), and from normal human brain were analyzed. Genomic DNA was extracted from E14 ES cells and embryoid bodies using the Qiagen DNeasy Blood and Tissue Kit (Qiagen, Valencia, Calif.). NIH 3T3 and Hela DNA were obtained from ATCC. DNA from human tissues was purchased from Biochain, Hayward, Calif. Five μg of genomic DNA was digested with 100 units MspI (NEB). Digested DNA was purified with phenol chloroform, and then 0.5 μg of digested DNA was mixed with 0.2 μg pCpG-MspI-9 plasmid, linearized at the single MspI site on the plasmid, and incubated with 2000 units T4 DNA ligase. The ligation mixture was glucosylated with 32 units BGT (NEB) and 0.5 mM UDP-Glc, the cofactor (NEB). This sample was spin column purified, and again digested with 150 units MspI to ensure complete digestion of all non-ghmC MspI sites. The mixture of linear and remaining circular DNA was used to transform GT115 (Invitrogen, now Life Technologies, Carlsbad, Calif.)) or ER2924 (NEB) competent *E. coli* cells, promoting the selective degradation and elimination of the linear products. Transformed cells were selected via zeocin resistance conferred by the vector, and were expected to have inserts containing genomic DNA flanked by two MspI sites. Colonies present on rich media supplemented with 50 μg/ml zeocin were picked, grown in 5 ml rich broth with 50 μg/ml zeocin, plasmid was purified with Qiagen miniprep kits, and then sequenced at the NEB sequencing facility using Sanger sequencing methods. Derived sequences were aligned to the appropriate genome with NCBI Blast software. In each case, inserts were flanked by CCGG sites and contained sequences found in the reference genome, either mouse (Table 5) or human (Table 6). These putative hmC-containing DNA sequences included repetitive DNA elements and intergenic regions (Tables 5 and 6), showing a broad hmC distribution in the genome.

TABLE 5 hmC genomic loci in mouse tissue

| # of clones | # MspI sites | Gene | Information |
|---|---|---|---|
| 2 | 2 | Intergenic | Mouse Chromosome 10: bp 34574152 |
| 2 | 2 | Intergenic | Mouse Chromosome 11: bp 33898156 |
| 1 | 2 | Intergenic | Mouse Chromosome 12: bp 17432255 |
| 1 | 2 | Cyclin F | Intronic region: bp 1073249 |
| 1 | 2 | Intergenic | Mouse Chromosome 2: p 12557113 |
| 1 | 2 | Mxra7 | Intronic region: bp 28228129 |
| 1 | 2 | Lrp1 | Intronic region: bp 2372508 |
| 1 | 2 | Intergenic | Mouse Chromosome 8: bp 48334398 |
| 1 | 2 | Intergenic | Mouse Chromosome 11: bp 25210706 |
| 1 | 2 | Intergenic | Mouse Chromosome 5: bp 10658147 |
| 1 | 2 | Intergenic | Mouse Chromosome 13: bp 3661176 |
| 3 | 1 | Krt18 | Intronic region: bp 63148003 |
| 2 | 1 | Intergenic | Mouse Chromosome 13: bp 4870651 |
| 1 | 1 | Kirrel3 | Intronic region: bp 36276208 |
| 1 | 1 | Intergenic | Mouse Chromosome 15: bp 54727587 |

TABLE 6 hmC genomic loci from human tissue

| # of clones | # MspI sites | Gene | Information |
|---|---|---|---|
| 3 | 1 | Unknown | Aligns to several chromosomes |
| 3 | 2 | ATXN2 | Ataxin 2 |
| 3 | 2 | INPP4A | inositol polyphosphate-4-phosphatase, type I |
| 3 | 2 | PRKAA2 | protein kinase, AMP-activated, alpha 2 catalytic subunit |
| 3 | 3 | RPL11P5 | ribosomal protein L11 pseudogene 5 |
| 3 | 2 | THRAP3 | thyroid hormone receptor associated protein 3 |
| 3 | 2 | TTLL10 | tubulin tyrosine ligase-like family, member 10 |
| 2 | 2 | BCR | Breakpoint cluster region |
| 2 | 1 | DDHD1 | DDHD domain containing 1 |
| 2 | 1 | Intergenic | Human Chromosome 16, bp 574535550 |
| 2 | 1 | Intergenic | Human Chromosome 16, bp 2037850 |
| 2 | 3 | Intergenic | Human Chromosome 1, bp 229203550 |
| 2 | 2 | Intergenic | Human Chromosome 5, bp 68477050 |
| 2 | 2 | KPNA6 | karyopherin alpha 6 (importin alpha 7) |
| 2 | 1 | SND1 | staphylococcal nuclease and tudor domain containing 1 |
| 1 | 2 | Unknown | Aligns to several chromosomes |
| 1 | 2 | Unknown | *Homo sapiens* Chromosome 1 |
| 1 | 2 | Unknown | Aligns to several chromosomes |
| 1 | 2 | Unknown | *Homo sapiens* chromosome 1 |
| 1 | 2 | Unknown | Aligns to several chromosomes |
| 1 | 2 | Unknown | Aligns to several chromosomes |
| 1 | 2 | Unknown | Aligns to several chromosomes |
| 1 | 3 | Unknown | Aligns to several chromosomes |
| 1 | 2 | Unknown | Aligns to several chromosomes |
| 1 | 1 | ATP8A2 | ATPase, aminophospholipid transporter, class I, type 8A, member 2 |
| 1 | 1 | AUTS2 | AUTS2 autism susceptibility candidate 2 |
| 1 | 3 | BANP | BTG3 associated nuclear protein |
| 1 | 5 | CACNA1H | calcium channel, voltage-dependent, T type, alpha 1H subunit |
| 1 | 2 | CHID1 | chitinase domain containing 1 |
| 1 | 2 | DPM3 | dolichyl-phosphate mannosyltransferase polypeptide 3 |
| 1 | 2 | EGFR | epidermal growth factor receptor |
| 1 | 2 | Intergenic | Human Chromosome 3, bp 196319050 |
| 1 | 2 | Intergenic | Human Chromosome 9, bp 102235809 |
| 1 | 2 | Intergenic | 3kb upstream of COP9 constitutive photomorphogenic homolog |

TABLE 6-continued hmC genomic loci from human tissue

| # of clones | # MspI sites | Gene | Information |
|---|---|---|---|
| | | | subunit 6 (*Arabidopsis*) |
| 1 | 4 | Intergenic | Human Chromosome 5, bp 13600000 |
| 1 | 2 | Intergenic | Human Chromosome 18, bp 44237300 |
| 1 | 1 | Intergenic | Human Chromosome 3, bp 8482970 |
| 1 | 1 | Intergenic | Human Chromosome 2, bp 95649950 |
| 1 | 1 | LMF1 | lipase maturation factor 1 |
| 1 | 3 | NASP | nuclear autoantigenic sperm protein (histone-binding) |
| 1 | 2 | NT5DC2 | 5'-nucleotidase domain containing 2 |
| 1 | 1 | RALGAPB | Ral GTPase activating protein, beta subunit (non-catalytic) |
| 1 | 2 | Repetitive element | Alu |
| 1 | 2 | Repetitive element | Alu |
| 1 | 2 | Repetitive element | Alu |
| 1 | 2 | Unkown | Human Chromosome 15 |
| 1 | 3 | RTN4RL1 | reticulon 4 receptor-like 1 |
| 1 | 2 | TCF7L2 | transcription factor 7-like 2 (T-cell specific, HMG-box) |
| 1 | 3 | VANGL1 | vang-like 1 (van gogh, *Drosophila*) |

Example 12

Measuring the Presence of hmC in Different Tissues

The identification of hmC-containing loci permitted identification, mapping and quantification of genomic loci that contained hmC in tissue samples. In the first case, hmC loci were surveyed to determine relative abundance. Loci recovery was proportional to the fraction of those loci within the sample containing the hmC modification. Determination of mC and hmC levels at a specific loci in a sample relied on the differential cleavage of C, mC, and hmC (or equivalently, ghmC) by selected site-specific endonucleases. Here, the isoschizomer pair, HpaII and MspI was used to fragment genomic DNA, as well as genomic DNA that had been glucosylated using BGT and UDP-Glc. Following fragmentation, resistance to cleavage was assayed by a site-specific PCR that traversed the interrogated locus. A cartoon of expected PCR products is given in FIG. 11. To simplify analysis, PCR primers were chosen such that they flanked a single test CCGG site, and such that a unique PCR product was derived from the undigested genomic DNA sample. While the length of the PCR product varied, fragments of 100-300 bp were desirable to facilitate amplification yields.

Mouse loci #2, 3, 4 and 12 were identified in experiments detailed in Example 11. Flanking sequences were used to develop PCR primers to amplify the CCGG site defining each locus (Table 7). Analysis of the methylation status of these four loci used the modification and digestion protocol presented in Example 11.

DNA of differentiated tissue derived from mouse brain, liver, heart, and spleen were obtained from Biochem USA, (Port St. Lucia, Fla.). DNA from cultured mouse fibroblast cell line NIH3T3 was prepared by using the Easy DNA Kit (Life Technologies, Carlsbad, Calif.).

Glucosylation and Digestion of Genomic DNA with Glucosyl Transferase and MspI or HpaII Two to five µg aliquots of genomic DNA were either glucosylated with 100 units of BGT in the presence of 0.5 mM UDP-Glc, or mock treated with BGT in the absence of UDP-Glc, for at least 3 hours. These reactions were then split in two (no UDP-Glc) or three (with UDP-Glc) parts. One of each was digested separately with MspI and HpaII, with the last aliquot reserved as mock-treated control.

Both digested and undigested DNAs were diluted to a final concentration of 16 ng/µl for PCR analysis. Endpoint PCR employed the Phusion-GC (NEB) Polymerase Master Mix. Two µl of the diluted DNAs described above were used for each 50 µl PCR reaction. Half of each PCR reaction was run on a 1.2% agarose gel (VWR, West Chester, Pa.), stained with ethidium bromide (Sigma-Aldrich, St. Louis, Mo.), and illuminated with UV light to visualize DNA bands.

The absence of a PCR band observed in some samples in FIG. 13 correlated with cleavage by the restriction endonuclease MspI. Conversely, the appearance of PCR product reflected resistance to endonuclease cleavage. Although nicking occurred on the unmodified strand in some instances of hemi-modification, this did not prevent amplification from the protected strand, leading to the pattern outlined. The expected pattern of PCR products for C modification within the CCGG site is presented in FIG. 12.

The results showed that brain DNA was substantially hydroxymethylated at all tested loci, indicated by an increased intensity of the DNA band observed in lane 3 over lane 1 (FIG. 13). The other mouse tissues displayed variable or undetectable amounts of hmC at the four loci. Locus #12 displayed some hmC in heart and liver, though less than in brain. The cultured NIH3T3 cells did not display detectable amounts of hmC at any of the loci tested (FIG. 13).

TABLE 7

Primers used for hydroxymethyl loci PCR analysis

| Locus # | Genomic position/Gene | Forward Primer sequence | Reverse Primer sequence |
|---|---|---|---|
| 2 | Chr. 10, bp 34574152 | GAACAGCAGAGGGAGATAG (SEQ ID NO: 1) | CAAGCCTGGAGTTAAGAGAG (SEQ ID NO: 2) |
| 3 | Chr. 10, bp 34574152 | GTGTGTTCTCCACCAAGTGT (SEQ ID NO: 3) | CTTTCTTCTCCCAGCATCAG (SEQ ID NO: 4) |

TABLE 7-continued

Primers used for hydroxymethyl loci PCR analysis

| Locus # | Genomic position/Gene | Forward Primer sequence | | Reverse Primer sequence | |
|---|---|---|---|---|---|
| 4 | Chr. 12, bp 17432255 | ATACAGTGGCTTGGGAGAGG | (SEQ ID NO: 5) | GTGACATAGACTGAGAGGAGAC | (SEQ ID NO: 6) |
| 12 | Chr. 2, Lrp1, Intron, bp 2372508 | TCCTTACCCTGAATGACTCC | (SEQ ID NO: 7) | CAACCCACACTATTCCCTTG | (SEQ ID NO: 8) |

The significance of the analysis of individual loci described above was further substantiated by looking at total genomic hydroxymethylation.

When the total amount of methylation and hydroxymethylation in cells using the above techniques and adding the results for hmC to the results of mC was examined, it was found that the total was similar to the total obtained by bisulfite sequencing, which was unable to discriminate between hmC and mC. The results are shown in Table 8 and FIG. 17.

The above methods can be used for evaluating the status of hydroxymethylation in loci that have been validated as biomarkers biomarkers in tissue from patients for medical prognosis and diagnosis and disease progression studies.

TABLE 8

The relative amounts of total hmC and mC in the cell genome using the methods above and comparing the results with bisulpfite sequencing (see FIG. 17)

| Total methylation: | Brain | Liver | Heart | Spleen |
|---|---|---|---|---|
| hmC Locus Detection Kit | 80% | 81% | 94% | 98% |
| Bisulfite sequencing | 80% | 92% | 93% | 92% |

Example 13

Measuring the Presence of hmC During Development

The procedure of Example 12 was used to examine the dynamics of hmC and mC in embryonic stem cells at various stages of differentiation.

ES14 cells were cultured in GMEM (Gibco, Invitrogen, now Life Technologies, Carlsbad, Calif.) media containing 10% FBS (Gemcell), 1% NEAA (Hyclone, now Thermo Scientific, Rockford, Ill.), 1% sodium pyruvate (Gibco), 50 μM β-mercaptoethanol (Sigma-Aldrich, St. Louis, Mo.), and 1× Leukemia Inhibitory Factor (LIF) (Millipore, Billerica, Mass.). Undifferentiated ES cells were grown and maintained on 0.1% Gelatin (Stem Cell Technologies, Vancouver, BC) coated culture dishes. For differentiation of ES cells to embryoid bodies, LIF was removed and cells were seeded on low adherence plates (Corning, Corning, N.Y.) with no gelatin for 1 to 10 days (Keller Curr. Opin. Cell Biol. 7 (1995); Hopfl et al. Methods Mol. Biol. 254 (2004)).

Validation of the differentiation protocol was obtained by monitoring expression of totipotent ES markers Oct4 and Nanog by Western blot analysis. After LIF withdrawal, both proteins were down-regulated, as expected.

The extent of mC and hmC at four genomic loci was explored as in Example 12 using DNA extracted from ES14 cells harvested at various times after withdrawal of supporting cytokines, marked by withdrawing LIF from the media. FIG. 14 illustrates changes in modification of loci 2, 3, 4, and 12 during differentiation. Interestingly, in locus #2, the sample at time 0 contained hmC (a band present in the third lane) but by 7 days, it was depleted, not modifiable by BGT and thus sensitive to cleavage by MspI, resulting in no amplicon. At locus #3, the hmC site was lost at 10 days, at locus #4 at 5 days, and at locus #12, loss of hmC occurred around 1 day.

Example 14

Quantitative Analysis of the Level of hmC During Development qPCR can be used to determine the relative copy numbers of different cell states and for determining the quantity of starting template. This provided a value for the absolute quantity of DNA that was intact or digested in the above analysis.

Samples from Example 13 locus #3 were additionally subjected to quantitative PCR using Dynamo HS SYBR green qPCR Kit (NEB) and a Biorad (Hercules, Calif.) CFX384 Real-Time PCR Detection System. The copy number derived from this analysis was corrected for the background signal, and then normalized to undigested control, in this case mock-glucosylated undigested DNA (experimental amplicon/undigested DNA amplicon)*100). Results are presented in FIG. 15.

Example 15

HmC Locus Detection Kit for Detection and Quantitation of hmC in CCGG Sites

The following describes a specific implementation of the method of Examples 13 and 14. Each kit (see Table 9) contains sufficient reagents for 50 reactions.

TABLE 9

Kit components

| Component | Contents | Concentration |
|---|---|---|
| T4 BGT | 1 × 60 μl | 10 U/μl |
| UDP-Glc | 1 × 100 μl | 50x (2 mM) |
| MspI | 1 × 50 μl | 100 U/μl |
| HpaII | 1 × 100 μl | 50 U/μl |
| Proteinase K | 1 × 100 μl | 20 mg/ml |
| NEBuffer 4 | 1 × 500 μl | 10X |
| Instruction Manual | | |
| Optionally reagents for PCR | | |

PCR Materials:
Locus-specific primers, flanking a CCGG site of interest
A PCR polymerase
Nucleotides for PCR
PCR Thermal Cycler (for endpoint experiments)
Real-time PCR cycler (for quantitative experiments)

Method Overview Contained in Instructions

The hmC locus detection kit distinguishes 5-mC from 5-hmC by adding glucose to the hydroxyl group of 5-hmC using BGT. When the hmC occurs in the context of CCGG, this modification converts a cleavable MspI site to a non-cleavable one.

The hmC locus detection kit has the following features:
Converts substantially all hmC into ghmC in DNA.
Allows discrimination between 5mC and hmC in CCGG sequences using PCR amplification and enzyme digestion.
The procedure is simple, reliable, and gives consistent results
No expertise beyond accurate and pipetting technique is required.

The 5hmC locus detection kit was designed for the detection and relative quantification of 5hmC in double-stranded DNA (dsDNA) containing a CpG site in the MspI/HpaII (CCGG) recognition sequence. The kit provides materials for 50 reactions. The procedure is summarized in FIG. 11. The 5hmC locus detection is based on classical methods of methylation analysis using the differential sensitivity of some isochizomeric restriction enzymes to methylation of DNA, notably, the MspI/HpaII pair. Both enzymes recognize the CCGG sequence and cut unmethylated sites. HpaII is unable to cut DNA when the internal cytosine is methylated or hydroxymethylated, whereas MspI will still cut. But MspI will not cut when the internal hmC is glucosylated with T4 BGT enzyme.

Step I: DNA Glucosylation Reaction (T4 BGT)

Genomic DNA of interest is treated with BGT in order to modify hmC by glucosylation. This reaction is sequence-independent—all hmC will be glucosylated.

TABLE 10

Glucosylation of hmC in DNA

| Reaction Component | Volume, μl | Stock | Final Concentration |
| --- | --- | --- | --- |
| Genomic DNA | 18.6 | 500 μg/ml | 30 μg/ml |
| UDP-Glc | 12.4 | 1 mM (25x) | 40 μM |
| NEBuffer 4 | 31.0 | 10x | 1x |
| Nuclease-free water | 248.0 | | Total volume: 310 μl |

Mix the components listed in Table 10 in a 1.5 ml reaction tube. Split the reaction mixture into two tubes (155 μl each). Add 30 units (3 μl) of BGT into one tube. The second tube is a control with no BGT added. Incubate both tubes at 37° C. from 12 to 18 hours.

Step II: Restriction Endonuclease Digestion

MspI and HpaII, recognize the same sequence (CCGG), but have different methylation sensitivities. HpaII cleaves only a completely unmodified site, i.e., any modification (mC, hmC or ghmC) at either cytosine blocks cleavage (results 3, 4, 7 and 8 in FIG. 11). MspI can still cleave when the internal C residue is methylated or hydroxymethyated (results 2, 5 and 6 in FIG. 11), but will not cut if it is glucosylated (result 1), or when the external C is modified. In most metazoans, cytosine methylation occurs primarily in the context of CpG, so in CCGG sites, HpaII will not cut modified sites.

Equally divide each reaction mixture into three 0.2 ml PCR-strip tubes (total 6 tubes, 50 ml each). Add 100 units (1 μl) of MspI, into Tube No. 1 and Tube No. 4. Add 50 units (1 μl) of HpaII into Tube No. 2 and Tube No. 5. Tubes No. 3 and No. 5 are controls, no restriction enzyme added. Incubate the reactions at 37° C. for 4 h. Optionally, add 1 μl of Proteinase K into each tube and incubate at 40° C. for 30 minutes. Heat inactivate Proteinase K by incubating at 95° C. for 10 minutes.

Step III: Interrogation of the Locus by PCR (See Table 11)

As little as 20 ng of input DNA can be used. Amplify the experimental (glucosylated and digested) and control (mock-glucosylated, and digested) target DNA with primers flanking a CCGG site of interest designed to yield products between 100-200 bp. If the CpG site contains 5-hmC, a band will be seen after glucosylation and digestion, but not in the control non-glucosylated sample (see FIG. 11). qPCR will give an approximation of how much hmC is in this particular site (see FIGS. 16 and 17).

TABLE 11

End Point PCR/qPCR

| PCR Component | 25 μl PCR Reaction | 50 μl PCR Reaction | Final Concentration |
| --- | --- | --- | --- |
| 5X LongAmp Taq Reaction Buffer | 5 μl | 10 μl | 1X |
| 10 mM dNTPs | 0.75 μl | 1.5 μl | 300 μM |
| 10 μM Forward Primer | 0.5 μl | 1 μl | 0.4 μM (0.05-1 μM) |
| 10 μM Reverse Primer | 0.5 μl | 1 μl | 0.4 μM (0.05-1 μM) |
| Template DNA | 1.5 μl | 3 μl | 150 ng |
| LongAmp Taq DNA Polymerase | 0.5 μl | 1 μl | 5 U/50 μl PCR |
| Nuclease-free water | Up to 25 μl | Up to 50 μl | |

Real Time PCR

For real time PCR, use 1-2 μl (30-60 ng) of template (from Step 2, after restriction endonuclease digestion) and follow the manufacturer's recommendations.

If using a standard curve to determine copy number, samples can be normalized by dividing the copy number of samples No. 1-5 by the copy number of the control undigested sample (No. 6). If using the comparative Ct method, samples can be normalized by setting the control undigested sample (No. 6) as the calibrator. This normalization will give an approximate percentage of unmethylated, methylated (HpaII-digested samples, No. 2 & 5) and hydroxymethylated (BGT- and MspI-digested sample, No. 1) alleles in the sample.

Estimation of the Relative Percentage of Unmodified Cytosine (C), mC, hmC on the CCGG Site Based on the qPCR results, a simplified scheme is provided to calculate the relative percentage of C, mC and hmC.

$$C^{hm}CGG\% = (M_2 - M_1)/C_1;$$

$$C^{m}CGG\% = (H_1 - M_2)/C_1;$$

$$CCGG\% = (C_1 - H_1)/C_1.$$

In these calculations, the parameters are:
$M_1$: qPCR value* in the sample of genomic DNA with MspI.
$M_2$: qPCR value in the sample of genomic DNA with MspI and BGT.
$C_1$: qPCR value in the sample of genomic DNA with BGT only.
$H_1$: qPCR value in the sample of genomic DNA with HpaII and BGT.
*: qPCR value can be raw Ct values or normalized Ct values. The derivation of these formulas is based on the following:
Assume for a specific CCGG site to be interrogated, $N_1$: population (copy number) of CCGG site (unmodified)
$N_2$: population of $C^mCGG$ site
$N_3$: population of $C^{hm}CGG$ site
$N_4$: population of intrinsically MspI-resistant sites, which includes noncanonical modification patterns: $^mCCGG$, $^{hm}C$-CGG, $^mC^mCGG$, $^{hm}C^{hm}CGG$ but not $C^mCGG$ or $C^{hm}CGG$. These resistant modification patterns are thought to be rare in metazoans.

In experiment with MspI, we have:

$k*M_1=N_4$, assume $k$ is a constant for all qPCR experiments.     i $k*M_2=N_3+N_4$     ii In experiment with HpaII, we have:

$k*H_1=N_2+N_3+N_4$     iii

In experiment with BGT only, we have:

$k*C_1=N_1+N_2+N_3+N_4$     iv

Thus, for the specific CCGG:

Based on (eq i) & (eq ii), $C^{hm}CGG\%=N_3/(N_1+N_2+N_3+N_4)=(M_2-M_1)/C_1$;

Based on (eq ii) & (eq iii), $C^mCGG\%=N_2/(N_1+N_2+N_3+N_4)=(H_1-M_2)/C_1$;

Based on (eq iii) & (eq iv), $CCGG\%=N_1/(N_1+N_2+N_3+N_4)=(C_1-H_1)/C_1$.

Example 16

Ultra High Throughput hmC Loci Detection Kit Using One or More Enzymes from the MspJI Family Each kit may contain a glucosyltransferase, and additionally as required, a UDP-Glc, MspJI, optionally an activator and a buffer such as NEBuffer #4 and an instruction manual.

The hmC loci detection kit includes the following features. The kit: substantially converts all hmC into glucosylated hmC in DNA; allows enrichment of hmC containing 32-mer fragments for high throughput sequencing and optionally can be sequenced on a ultra high throughput sequencing platforms using selected adaptors.

Total methylome library is constructed using a NextGen-sequencing adaptor from any supplier such as Illumina/SOLiD. After ligation of the adaptor, the ligated DNA is reacted with BGT and UDP-Glc and another round of MspJI cleavage is performed to enrich hmC-specific clones as described in Examples 7 and 8.

Example 17

Calculation of the Levels of hmC/mC at Specific Loci Using MspJI-Like Enzymes

Examples described above, such as Examples 10 and 12, provide methods of quantifying the relative amounts of C/hmC/mC at a single nucleotide site using MspI and BGT. MspJI-like enzymes and glucosyltransferases can be used for the same purpose in loci containing MspJI-like recognition sites. The advantage is that MspJI-like enzymes are not restricted to the CCGG site. The quantification of the cleavage at recognition sites can be revealed by qPCR or any other standard techniques. Specific primers for qPCR, both upstream and downstream to the specific locus containing the recognition sites, can be designed based on known genome sequences. It is suggested that three qPCR readings, one from MspJI-digested genomic DNA sample, one from MspJI-digested glucosylated genomic DNA sample, one from undigested genomic DNA sample, should be made. Internal controls, such as DNA fragments containing same recognition site, with 5mC or with 5hmC, can be spiked into the genomic DNA sample as a way to estimate the level of completion of the cleavage. These controls may also be run externally in separate tubes. For the simplicity of the analysis, the MspJI cleaves x % of the recognition site containing 5mC and y % of the recognition site containing 5hmC. N(C) is the population of recognition sites with regular cytosine and the same for N(5mC), N(5hmC) etc.

$$k*M1 = N(C) + x\%*N(5mC) + y\%*N(5hmC) \quad (1)$$

$$k*M2 = N(C) + x\%*N(5mC) + N(5hmC) \quad (2)$$

$$k*M3 = N(C) + N(5mC) + N(5hmC) \quad (3)$$

From (1) and (2), we have:

$5hmC\% = (M2-M1)/[(1-y\%)*M3]$;

$5mC\% = (M3-M2)/[(1-x\%)*M3]$;

$C\% = 1 - 5mC\% - 5hmC\%$.

Using the approach outlined above, C/mC/hmC can be determined at any individual position for the nucleotide and the ratio calculated at any locus of interest. This information can then be used for comparative studies to determine characteristic percentages of hmC at a locus of interest to permit correlations with phenotype. Similarly changes in characteristic percentages of hmC within a locus can be determined at different time points to determine intraperson variation or interperson variation.

Example 18

Automation of the Processes Described Herein for High Throughput Analysis

The reagents and protocols described herein are suited for automation. Wet chemistry may be performed using a microfluidic device or chip-based array or other arrays such as are well known in the art. The results from these platforms may be read by means of any of the detection methods that are standard in the art using, for example, fluorescence detection to identify positive samples.

Wet chemistry, or indeed equivalent solid phase reactions, can be achieved in a suitable device, and the results interpreted in a user-friendly form by a second device, or alternatively these functions may be performed in a single device. For example, it is envisioned that the positions of individual hmNs and the identification of loci can be performed by a computer which further may compare the data obtained therefrom with a database of similar data. The data can then be added to the database to increase its comprehensiveness. Moreover, the computer may store phenotypic data correlated to certain hydroxymethylation patterns such that predictions can be made with suitable probabilistic caveats for diagnostic or therapeutic applications.

Example 19

Correlation of Changes in hmC Levels with Disease and Developmental States

The methods provided herein enable discovery of hmC loci and quantification of the extent of hmC present at those loci.

This allows correlative studies to analyze the association of that modified base on a variety of cellular and organism phenotypes. For example, the correlation of hmC modification with gene expression patterns, development, or disease establishment and progression holds the promise of illuminating the mechanism of hmC effects on these states. Furthermore, such correlative studies could provide new biomarkers for disease diagnosis, and subsequent treatment.

The first step in correlative studies is the establishment of a genome map of sites subject to hmC modification. Discovery of such sites can be accomplished using any of several approaches outlined above. Discovery will necessarily involve a variety of tissue samples at different developmental stages, as well as healthy and diseased tissues. Candidate loci are identified by comparison of the derived sequences with a reference genome, for example UCSC hg18 (NCBI Build 36) which is a reference assembly for all human DNA sequence, using bioinformatic methods known in the art. Once candidate loci are identified, levels of hmC, as well as mC, can be determined using techniques described above, including qPCR, and deep sequencing. The so-called CpG islands and CG-rich regions are thought to have particular importance in epigenetic control, and thus may be a particular area of focus.

Preferably, data will be accumulated for multiple samples derived from tissues, which are in turn derived from different individuals, but manifesting similar phenotypes.

hmC-annotated and mapped data between various tissues types may be compared for biomarker discovery. For this approach, DNA samples from diseased and matched healthy tissues and/or cells at different developmental stages, including stem cells, may be analyzed and compared. A large number of samples for a specific disease (such as brain disease, or any variety of cancer types) may be evaluated in parallel. Significant and consistent differences in the levels of hmC at specific loci among samples displaying different phenotypes identify loci that can serve as markers of differentiation state, or of healthy versus diseased states. Such loci have the potential of indicating a changed state prior to the manifestation of phenotype. For example, changes in hmC may precede the actual manifestation of a disease state, and thus be useful in diagnosis and treatment of disease. Furthermore, correlations may allow further dissection of disease states into specific categories.

We claim:

1. A method of quantifying the amount of a hydroxymethylated nucleotide (hmN) in a polynucleotide preparation, comprising:
   (a) obtaining a preparation of polynucleotides;
   (b) modifying any hmN in the polynucleotides of a first portion of the preparation to produce modified hmN (mhmN), wherein the modifying is done using a DNA glucosyltransferase; and
   (c) quantifying the amount of hmN in the preparation by:
      (i) reacting the polynucleotides from (b) with a site-specific endonuclease selected from BccI, BciVI, BspHI, BspQI, BstEII, BstNI, BstYI, BstCI, CviAII, CviQI, DpnI, EcoRI, HinfI, Hpy188I, Hpy188III, MboII, MfeI, MlyI, NsiI, RsaI, ScaI, SfcI, SmlI, Tsp45I, XbaI, BsaWI, BsoBI, BspEI, BssI, BtgZI, EciI, MspI, NmeAII, PspXI, TliI, XhoI, and XmaI; and
      (ii) comparing the amount of an uncleaved polynucleotide that would otherwise be cleaved but for the modified hmN with the amount of uncleaved polynucleotide produced by digesting a control sample by the site-specific endonuclease, wherein the control sample is a second portion of the preparation that has not been modified to produce mhmN.

2. The method of claim 1, wherein the N, mN, hmN and mhmN are C, mC, hmC and mhmC respectively.

3. The method of claim 1, wherein the site-specific endonuclease is also capable of cleaving a polynucleotide at the specific recognition site comprising mN.

4. The method of claim 1, wherein the site-specific endonuclease is also capable of cleaving a polynucleotide at the specific recognition site when the nucleotide is a mN and when the nucleotide is a N.

5. The method of claim 1, further comprising distinguishing between an unmethylated nucleotide (N) and a methylated nucleotide (mN) in the polynucleotide preparation.

6. The method of claim 5, comprising reacting a control sample of the polynucleotide preparation with a second site-specific endonuclease, wherein the second site-specific endonuclease is capable of cleaving a polynucleotide at a specific recognition site containing the nucleotide when the nucleotide is a N, but not when the nucleotide is a mN or a hmN, and detecting a cleaved polynucleotide; and thereby determining that the nucleotide in the polynucleotide preparation is a N.

7. The method of claim 1, wherein an adapter is ligated to the polynucleotides in the sample for amplifying or sequencing an uncleaved polynucleotide.

8. The method of claim 1, wherein the method further comprises mapping an hmN detected in c) to a genomic locus.

9. The method of claim 1, wherein the polynucleotide preparation is derived from a cell, tissue or organism and wherein (c) comprises identifying an hmN at a predetermined locus in a genome for the polynucleotide in the preparation.

10. The method of claim 9, wherein the method comprises determining an amount of the hmN in the predetermined locus in the genome from a cell, tissue or organism.

11. The method of claim 1, wherein the method comprises comparing the amount of hmN in polynucleotides in a first polynucleotide preparation to the amount of hmN in polynucleotides in a second polynucleotide preparation.

12. The method of claim 1, further comprising correlating with a phenotypic trait, a difference in the amount of the hmN at a predetermined locus in a first polynucleotide in a first polynucleotide preparation and in a second polynucleotide in a second polynucleotide preparation.

13. The method of claim 1, wherein further comprising recording in a computer-readable form the amount of hmN measured in (c).

14. A method of quantifying the amount of a hydroxymethylated cytosine (hmC) in a polynucleotide preparation, comprising:
   (a) obtaining a preparation of polynucleotides;
   (b) modifying any hmC in the polynucleotides of a first portion of the preparation to produce modified hmC (mhmC), wherein the modifying is done using a DNA glucosyltransferase; and
   (c) quantifying the amount of hmC in the preparation by:
      (i) reacting the polynucleotides from (b) with MspI; and
      (ii) comparing the amount of an uncleaved polynucleotide that would otherwise be cleaved but for the mhmC with the amount of uncleaved polynucleotide produced by digesting a control sample by MspI, wherein the control sample is a second portion of the preparation that has not been modified to produce mhmC.

* * * * *

SEQUENCE LISTING

```
<160> NUMBER OF SEQ ID NOS: 49

<210> SEQ ID NO 1
<211> LENGTH: 19
<212> TYPE: DNA
<213> ORGANISM: artificial
<220> FEATURE:
<223> OTHER INFORMATION: primer

<400> SEQUENCE: 1
gaacagcaga gggagatag                                                   19

<210> SEQ ID NO 2
<211> LENGTH: 20
<212> TYPE: DNA
<213> ORGANISM: artificial
<220> FEATURE:
<223> OTHER INFORMATION: primer

<400> SEQUENCE: 2
caagcctgga gttaagagag                                                  20

<210> SEQ ID NO 3
<211> LENGTH: 20
<212> TYPE: DNA
<213> ORGANISM: artificial
<220> FEATURE:
<223> OTHER INFORMATION: primer

<400> SEQUENCE: 3
gtgtgttctc caccaagtgt                                                  20

<210> SEQ ID NO 4
<211> LENGTH: 20
<212> TYPE: DNA
<213> ORGANISM: artificial
<220> FEATURE:
<223> OTHER INFORMATION: primer

<400> SEQUENCE: 4
ctttcttctc ccagcatcag                                                  20
```

```
<210> SEQ ID NO 5
<211> LENGTH: 20
<212> TYPE: DNA
<213> ORGANISM: artificial
<220> FEATURE:
<223> OTHER INFORMATION: primer

<400> SEQUENCE: 5
atacagtggc ttgggagagg                                                    20

<210> SEQ ID NO 6
<211> LENGTH: 22
<212> TYPE: DNA
<213> ORGANISM: artificial
<220> FEATURE:
<223> OTHER INFORMATION: primer

<400> SEQUENCE: 6
gtgacataga ctgagaggag ac                                                 22

<210> SEQ ID NO 7
<211> LENGTH: 20
<212> TYPE: DNA
<213> ORGANISM: artificial
<220> FEATURE:
<223> OTHER INFORMATION: primer

<400> SEQUENCE: 7
tccttaccct gaatgactcc                                                    20

<210> SEQ ID NO 8
<211> LENGTH: 20
<212> TYPE: DNA
<213> ORGANISM: artificial
<220> FEATURE:
<223> OTHER INFORMATION: primer

<400> SEQUENCE: 8
caacccacac tattcccttg                                                    20

<210> SEQ ID NO 9
<211> LENGTH: 33
<212> TYPE: DNA
<213> ORGANISM: artificial
<220> FEATURE:
<223> OTHER INFORMATION: primer

<400> SEQUENCE: 9
acactctttc cctacacgac gctcttccga tct                                     33

<210> SEQ ID NO 10
<211> LENGTH: 33
<212> TYPE: DNA
<213> ORGANISM: artificial
<220> FEATURE:
<223> OTHER INFORMATION: primer

<400> SEQUENCE: 10
gatcggaaga gctcgtatgc cgtcttctgc ttg                                     33

<210> SEQ ID NO 11
<211> LENGTH: 35
<212> TYPE: DNA
<213> ORGANISM: artificial
<220> FEATURE:
<223> OTHER INFORMATION: primer
```

<400> SEQUENCE: 11
acactctttc cctacacgac gctcttccga tctgg                          35

<210> SEQ ID NO 12
<211> LENGTH: 35
<212> TYPE: DNA
<213> ORGANISM: artificial
<220> FEATURE:
<223> OTHER INFORMATION: primer

<400> SEQUENCE: 12
cagatcggaa gagctcgtat gccgtcttct gcttg                          35

<210> SEQ ID NO 13
<211> LENGTH: 38
<212> TYPE: DNA
<213> ORGANISM: artificial
<220> FEATURE:
<223> OTHER INFORMATION: primer

<400> SEQUENCE: 13
acactctttc cctacacgac gctcttccga tctcacgg                       38

<210> SEQ ID NO 14
<211> LENGTH: 38
<212> TYPE: DNA
<213> ORGANISM: artificial
<220> FEATURE:
<223> OTHER INFORMATION: primer

<400> SEQUENCE: 14
cgtgagatcg gaagagctcg tatgccgtct tctgcttg                       38

<210> SEQ ID NO 15
<211> LENGTH: 38
<212> TYPE: DNA
<213> ORGANISM: artificial
<220> FEATURE:
<223> OTHER INFORMATION: primer

<400> SEQUENCE: 15
acactctttc cctacacgac gctcttccga tcttatgg                       38

<210> SEQ ID NO 16
<211> LENGTH: 38
<212> TYPE: DNA
<213> ORGANISM: artificial
<220> FEATURE:
<223> OTHER INFORMATION: primer

<400> SEQUENCE: 16
cataagatcg gaagagctcg tatgccgtct tctgcttg                       38

<210> SEQ ID NO 17
<211> LENGTH: 16
<212> TYPE: DNA
<213> ORGANISM: artificial
<220> FEATURE:
<223> OTHER INFORMATION: primer

<400> SEQUENCE: 17
atggtcmagg agccag                                               16

<210> SEQ ID NO 18
<211> LENGTH: 16

```
<212> TYPE: DNA
<213> ORGANISM: artificial
<220> FEATURE:
<223> OTHER INFORMATION: primer

<400> SEQUENCE: 18
tggctcmtgg accatg                                                      16

<210> SEQ ID NO 19
<211> LENGTH: 19
<212> TYPE: DNA
<213> ORGANISM: artificial
<220> FEATURE:
<223> OTHER INFORMATION: oligonucleotide

<400> SEQUENCE: 19
acacccatca catttacac                                                   19

<210> SEQ ID NO 20
<211> LENGTH: 45
<212> TYPE: DNA
<213> ORGANISM: artificial
<220> FEATURE:
<223> OTHER INFORMATION: oligonucleotide

<400> SEQUENCE: 20
ccaactctac attcaactct tatccggtgt aaatgtgatg ggtgt                      45

<210> SEQ ID NO 21
<211> LENGTH: 45
<212> TYPE: DNA
<213> ORGANISM: artificial
<220> FEATURE:
<223> OTHER INFORMATION: primer

<400> SEQUENCE: 21
acacccatca catttacacc ggataagagt tgaatgtaga gttgg                      45

<210> SEQ ID NO 22
<211> LENGTH: 45
<212> TYPE: DNA
<213> ORGANISM: artificial
<220> FEATURE:
<223> OTHER INFORMATION: primer

<400> SEQUENCE: 22
ccaactctac attcaactct tatccggtgt aaaugtgatg ggtgt                      45

<210> SEQ ID NO 23
<211> LENGTH: 27
<212> TYPE: DNA
<213> ORGANISM: artificial
<220> FEATURE:
<223> OTHER INFORMATION: primer

<400> SEQUENCE: 23
ggttaattgg ccaaggtaac cagatag                                          27

<210> SEQ ID NO 24
<211> LENGTH: 45
<212> TYPE: DNA
<213> ORGANISM: artificial
<220> FEATURE:
<223> OTHER INFORMATION: primer

<400> SEQUENCE: 24
```

```
ccaactcuac aucaacucu uauccgguguaaaugugaug ggugu          45
```

<210> SEQ ID NO 25
<211> LENGTH: 45
<212> TYPE: DNA
<213> ORGANISM: artificial
<220> FEATURE:
<223> OTHER INFORMATION: primer

<400> SEQUENCE: 25

```
ccaactcuac aucaacucu uauccgguguaaaugugaug ggugu          45
```

<210> SEQ ID NO 26
<211> LENGTH: 37
<212> TYPE: DNA
<213> ORGANISM: artificial
<220> FEATURE:
<223> OTHER INFORMATION: primer

<400> SEQUENCE: 26

```
ccaactcaca tcaaccttac cgggtaaagt gaggggt                 37
```

<210> SEQ ID NO 27
<211> LENGTH: 24
<212> TYPE: DNA
<213> ORGANISM: artificial
<220> FEATURE:
<223> OTHER INFORMATION: primer

<400> SEQUENCE: 27

```
ccaactctac attcaactct tatc                               24
```

<210> SEQ ID NO 28
<211> LENGTH: 45
<212> TYPE: DNA
<213> ORGANISM: artificial
<220> FEATURE:
<223> OTHER INFORMATION: oligonucleotide

<400> SEQUENCE: 28

```
tcagtgaagt tggcagactg agccaggtcc cacagatgca gtgac        45
```

<210> SEQ ID NO 29
<211> LENGTH: 51
<212> TYPE: DNA
<213> ORGANISM: artificial
<220> FEATURE:
<223> OTHER INFORMATION: oligonucleotide

<400> SEQUENCE: 29

```
actccgguca ctgcatctgt gggacctggc tcagtctgcc aacttcactg a  51
```

<210> SEQ ID NO 30
<211> LENGTH: 51
<212> TYPE: DNA
<213> ORGANISM: artificial
<220> FEATURE:
<223> OTHER INFORMATION: oligonucleotide

<400> SEQUENCE: 30

```
tcagtgaagt tggcagactg agccaggtcc cacagatgca gtgaccggag t  51
```

<210> SEQ ID NO 31
<211> LENGTH: 51
<212> TYPE: DNA
<213> ORGANISM: artificial

<220> FEATURE:
<223> OTHER INFORMATION: oligonucleotide

<400> SEQUENCE: 31
actccgguca ctgcatctgt gggacctggc tcagtctgcc aacttcactg a          51

<210> SEQ ID NO 32
<211> LENGTH: 51
<212> TYPE: DNA
<213> ORGANISM: artificial
<220> FEATURE:
<223> OTHER INFORMATION: oligonucleotide

<400> SEQUENCE: 32
tcagtgaagt tggcagactg agccaggtcc cacagatgca gtgaccggag t          51

<210> SEQ ID NO 33
<211> LENGTH: 43
<212> TYPE: DNA
<213> ORGANISM: artificial
<220> FEATURE:
<223> OTHER INFORMATION: oligonucleotide

<400> SEQUENCE: 33
cactgcatct gtgggacctg gctcagtctg ccaacttcac tga                  43

<210> SEQ ID NO 34
<211> LENGTH: 59
<212> TYPE: DNA
<213> ORGANISM: artificial
<220> FEATURE:
<223> OTHER INFORMATION: oligonucleotide

<400> SEQUENCE: 34
accggaguca ttgccaaact ctgcaggaga gcaagggctg tctataggtg gcaagtcag   59

<210> SEQ ID NO 35
<211> LENGTH: 55
<212> TYPE: DNA
<213> ORGANISM: artificial
<220> FEATURE:
<223> OTHER INFORMATION: oligonucleotide

<400> SEQUENCE: 35
ctgacttgcc acctatagac agcccttgct ctcctgcaga gtttggcaat gactc       55

<210> SEQ ID NO 36
<211> LENGTH: 59
<212> TYPE: DNA
<213> ORGANISM: artificial
<220> FEATURE:
<223> OTHER INFORMATION: oligonucleotide

<400> SEQUENCE: 36
accggaguca ttgccaaact ctgcaggaga gcaagggctg tctataggtg gcaagtcag   59

<210> SEQ ID NO 37
<211> LENGTH: 59
<212> TYPE: DNA
<213> ORGANISM: artificial
<220> FEATURE:
<223> OTHER INFORMATION: oligonucleotide

<400> SEQUENCE: 37
ctgacttgcc acctatagac agcccttgct ctcctgcaga gtttggcaat gactccggt   59

<210> SEQ ID NO 38
<211> LENGTH: 51
<212> TYPE: DNA
<213> ORGANISM: artificial
<220> FEATURE:
<223> OTHER INFORMATION: oligonucleotide

<400> SEQUENCE: 38
cattgccaaa ctctgcagga gagcaagggc tgtctatagg tggcaagtca g         51

<210> SEQ ID NO 39
<211> LENGTH: 59
<212> TYPE: DNA
<213> ORGANISM: artificial
<220> FEATURE:
<223> OTHER INFORMATION: oligonucleotide

<400> SEQUENCE: 39
ctgacttgcc acctatagac agcccttgct ctcctgcaga gtttggcaat gactccggt    59

<210> SEQ ID NO 40
<211> LENGTH: 102
<212> TYPE: DNA
<213> ORGANISM: artificial
<220> FEATURE:
<223> OTHER INFORMATION: oligonucleotide

<400> SEQUENCE: 40
tcagtgaagt tggcagactg agccaggtcc cacagatgca gtgaccggag tcattgccaa    60
actctgcagg agagcaaggg ctgtctatag gtggcaagtc ag                     102

<210> SEQ ID NO 41
<211> LENGTH: 102
<212> TYPE: DNA
<213> ORGANISM: artificial
<220> FEATURE:
<223> OTHER INFORMATION: oligonucleotide

<400> SEQUENCE: 41
ctgacttgcc acctatagac agcccttgct ctcctgcaga gtttggcaat gactccggtc    60
actgcatctg tgggacctgg ctcagtctgc caacttcact ga                     102

<210> SEQ ID NO 42
<211> LENGTH: 45
<212> TYPE: DNA
<213> ORGANISM: artificial
<220> FEATURE:
<223> OTHER INFORMATION: oligonucleotide

<400> SEQUENCE: 42
ccaacuctac autcaacuct tauccggugt aaaugtgaug ggugt                  45

<210> SEQ ID NO 43
<211> LENGTH: 59
<212> TYPE: DNA
<213> ORGANISM: artificial
<220> FEATURE:
<223> OTHER INFORMATION: oligonucleotide

<400> SEQUENCE: 43
actgctggtt acagtgctgt aactatacga tagctatctg gttaggcatg gccctggta    59

<210> SEQ ID NO 44
<211> LENGTH: 16

```
<212> TYPE: DNA
<213> ORGANISM: artificial
<220> FEATURE:
<223> OTHER INFORMATION: oligonucleotide

<400> SEQUENCE: 44
ttaaggcctt ggcagt                                                   16

<210> SEQ ID NO 45
<211> LENGTH: 12
<212> TYPE: DNA
<213> ORGANISM: artificial
<220> FEATURE:
<223> OTHER INFORMATION: oligonucleotide

<400> SEQUENCE: 45
ccaaggcctt aa                                                       12

<210> SEQ ID NO 46
<211> LENGTH: 16
<212> TYPE: DNA
<213> ORGANISM: artificial
<220> FEATURE:
<223> OTHER INFORMATION: oligonucleotide

<400> SEQUENCE: 46
ccttggccaa ttaacc                                                   16

<210> SEQ ID NO 47
<211> LENGTH: 20
<212> TYPE: DNA
<213> ORGANISM: artificial
<220> FEATURE:
<223> OTHER INFORMATION: oligonucleotide

<400> SEQUENCE: 47
ggttaattgg ccaaggtaac                                               20

<210> SEQ ID NO 48
<211> LENGTH: 61
<212> TYPE: DNA
<213> ORGANISM: artificial
<220> FEATURE:
<223> OTHER INFORMATION: oligonucleotide

<400> SEQUENCE: 48
ttaaggcctt ggcagtgctg taactatacg atagctatct ggttaccttg gccaattaac   60
c                                                                   61

<210> SEQ ID NO 49
<211> LENGTH: 26
<212> TYPE: DNA
<213> ORGANISM: artificial
<220> FEATURE:
<223> OTHER INFORMATION: primer

<400> SEQUENCE: 49
ttaaggcctt ggcagtgctg taacta                                        26
```